United States Patent [19]
Zick

[11] Patent Number: 5,908,761
[45] Date of Patent: Jun. 1, 1999

[54] GALECTIN-8 AND GALECTIN-8-LIKE PROTEINS AND DNA MOLECULES CODING THEREFOR

[75] Inventor: Yahiel Zick, Carmey Yosef, Israel

[73] Assignee: Yeda Research and Development Co. Ltd., Rehovot, Israel

[21] Appl. No.: 08/647,960

[22] PCT Filed: Dec. 5, 1994

[86] PCT No.: PCT/US94/13679

§ 371 Date: May 30, 1996

§ 102(e) Date: May 30, 1996

[87] PCT Pub. No.: WO95/15175

PCT Pub. Date: Jun. 8, 1995

[30] Foreign Application Priority Data

Dec. 5, 1993 [IL] Israel ......................................... 107880

[51] Int. Cl.$^6$ ........................... C07H 19/00; C12P 21/06; C07K 1/00; C07K 16/00
[52] U.S. Cl. .................... 435/69.1; 536/23.1; 435/320.1; 435/252.3; 530/387.1; 530/387.9; 530/350
[58] Field of Search ........................... 536/23.1; 530/300, 530/388.1, 387.1, 387.9, 350; 435/69.4, 320.1, 252.3

[56] References Cited

FOREIGN PATENT DOCUMENTS

WO 86/02651   5/1986   WIPO .

OTHER PUBLICATIONS

Reeck et al (Cell, 50: 667), 1987.
Lewin, (Science, 237: 1570), 1988.
Burgess et al. J. Cell Bio, 111: 2129–2138, 1990.
Lazar et al Mol & Cell Bio, 8: 1247–1252, 1988.
Tao et al. J. Immunol, 1989, 143:2595–2601, 1989.
Cherayil et al (PNAS, 1990, 87: 7324–7328.
Perillo et al, Apoptosis of T cell mediated by galectin–1, *Nature*, vol. 378, pp. 736–739, Dec. 14, 1995.
Gitt et al, Sequence and Mapping of Galectin–5, a B–Galactoside–binding Lectin, Found in Rat Erythrocytes *Journal of Biological Chemistry*, vol. 270, No. 10, pp. 5032–5038, Mar. 10, 1995.
Madsen et al, Cloning, Expression, And Chromosome Mapping Of Human Galectin–7, *Journal of Biological Chemistry*, vol. 270, No. 11, pp. 5823–5829, Mar. 17, 1995.
N. Sharon, Lectin–carbohydrate complexes of plants and animals: an atomic view, *TIBS* 18, pp. 221–225, Jun. 1993.
Hirabayashi et al, Effect fo Amino Acid Substitution by Site–directed Mutagenesis on the Carbohydate Recognition and Stability of Human 14–kDa B–Galactoside–binding Lectin, *Journal of Biological Chemistry*, vol. 266, No. 35, pp. 23648–23653, Dec. 15, 1991.

Lobsanov et al, X–ray Crystal Structure of the Human Dimeric S–Lac Lectin, L–14–II, in Complex with Lactose at 2.9–A Resolution, *Journal of Biological Chemistry*, vol. 268, No. pp. 27034–20738, Dec. 25, 1993.
Tracey et al, Subunit Molecular Mass Assignment of 14,654 Da to the Soluble B–Galactoside–binding Lectin from Bovine Heart Muscle and Demonstration of Intramolecular Disulfide Bonding Associated with Oxidative Inactivation, *Journal of Biological Chemistry*, vol. 267, No. 15, pp. 10342–10347, May 25, 1992.
Cooper et al, Endogenous Muscle Lectin Inhibits Myoblast Adhesion to Laminin, *Journal of Cell Biology*, vol. 115, No. 5, pp. 1437–1448, Dec. 1991.
Wells et al, Identification of an Autocrine Negative Growth Factor: Mouse B–Galactoside–Binding Protein Is a Cytosstatic Factor and Cell Growth Regulator, Cell, vol. 64, pp. 91–97, Jan. 11, 1991.
Yamaoka et al, Overexpression Of A B–Galactoside Binding Protein Causes Transformation Of BALALB3T3 Fibrolast Cells, *Biochemical and Biophysical Research Communications*, vol. 179, No. 1, pp. 272–279, Aug. 30, 1991.
Pooirer et al, Expression of the L14 lectin during mouse embryogenesis suggests multiple roles during pre–and post–implantation development, *Development 115*, pp. 143–155, (1992).
Ochieng et al, Structure–Function Relationship of a Recominant Human Galactoside–Binding Protein, *Biochemstry* 1993, 32, pp. 4455–4460.
Hirabayashi et al, Evidence That Caenorhabditis elegans 32–kDa B–Galactoside–binding Protein Is Homologous to Vertebrate B–Galactoside–binding Lectins, *Journal of Biological Chemistry*, vol. 267, No. 22, pp. 15485–15490 Aug. 5, 1992.
Lamphere et al, Components of Signaling Pathways for Insulin and Insulin–Like Growth Factor–I in Muscle Myoblasts and Myotubes, *Endocrinology*, vol. 131, No. 5, pp. 2196–2202, Apr. 30, 1992.
Cooper et al, Evidence for Export of a Muscle Lectin from Cytosol to Extracellular Matrix and for a Novel Secretory Mechanism, *Journal of Cell Biology*, vol. 110, pp. 1681–1691, May 1990.
Lis et al, [44] Soy Bean (Glycine max) Agglutinin, *Methods Enzymol*, pp. 360–368, (1972).

*Primary Examiner*—Paula K. Hutzell
*Assistant Examiner*—Susan Ungar
*Attorney, Agent, or Firm*—Browdy and Neimark

[57] ABSTRACT

The invention relates to a new mammalian S-type lectin, termed galectin-8, and to galectin-8-like proteins, to fragments thereof, to DNA molecules coding therefor and to pharmaceutical compositions comprising said proteins. Galectin-8, a widely expressed protein of 35 kDa is shown to be implicated in regulation of cell growth, particularly in inhibition of cell proliferation.

9 Claims, 6 Drawing Sheets

FIG. 1

```
   1  AATTCCCCCCCTGGC TGGGGACAAGTTA TTACT TTGAGTAATCCTTAAA TGAAGAGTGGG   60
  61  TAAAGCCCAT ATACGG AAGAGAGACTCCAGTCAACAATATCAA TAAGTTG AAGAAGA AA A  120

121  ATGTTGTCC TTAAGC AATC TACAAAATA TCATCTATAACCCGACAATCCCC TATG TCAG T  180
      Met Leu Ser Leu Ser Asn  Leu Gln Asn  Ile   Ile Tyr Asn Pro Thr  Ile Pro Tyr Val  Ser

181  ACCA TTACTGAGCAGTTGAAGCCTGGCTCTTTGATCGTGATCCGTGGCCATGTT CC TAA A    240
      Thr Ile  Thr Glu  Gln Leu Lys Pro  Gly Ser Leu Ile  Val  Ile  Arg  Gly His Val  Pro Lys

241  GAT TCAGAAAGATTCCAAGTAGACTTTCAGCATGGCAACAGCCTGAAGCCGAGAGCT GAT    300
      Asp  Ser Glu Arg Phe Gln Val Asp Phe Gln His  Gly Asn  Ser Leu Lys  Pro Arg Ala Asp

301  GTGGCCTTCCAC TTTAACCCTCGCTTCAAAAGGTCCAACTGC ATTGTTTGTAAC ACACTG    360
      Val Ala Phe His  Phe Asn Pro Arg Phe Lys Arg Ser Asn Cys  Ile  Val Cys Asn Thr  Leu

361  ACAAATGAGAAATGGGGCTGGGAGGAGATCACCCACGACATGCCTTTCAGAAAAGAAAAG    420
      Thr Asn Glu Lys Trp  Gly Trp  Glu  Glu  Ile  Thr  His Asp Met Pro Phe Arg Lys Glu  Lys

421  TCCTTTGAG ATTGTGATCATG GTGCTAAAGAACAAA TTCCACGTGGCTGTGAATGGAAAG    480
      Ser Phe Glu  Ile  Val   Ile Met Val  Leu Lys  Asn Lys Phe His  Val Ala  Val Asn Gly Lys

481  CACATTCTGCTG TATGCCCACAGGATCAACCCAGAGAAGATAGACACACTGGGCATCTTC    540
      His  Ile Leu Leu Tyr Ala His  Arg  Ile  Asn Pro Glu Lys  Ile  Asp Thr Leu  Gly  Ile  Phe

541  GGCAAAGTGAACATTCAC TCCATCGGGTTCAGATTCAGCTCGGATTTA CAGAGTATGGAA    600
      Gly Lys Val Asn  Ile  His  Ser   Ile  Gly Phe Arg Phe Ser Ser Asp Leu  Gln Ser Met  Glu

601  ACA TCTACTCTGGGACTGACACAG ATAAGTAAAGAAAATATACAAAAGTCTGGCAAGCTC    660
      Thr  Ser Thr Leu  Gly Leu Thr  Gln   Ile  Ser Lys Glu Asn  Ile  Gln Lys Ser  Gly Lys Leu

661  CAT TTGAGCCTGCCATTTGAAGCAAGGTTGAATGCCTCCATGGGCCCTGGACGAACCGTT    720
      His Leu Ser Leu  Pro Phe Glu Ala  Arg Leu Asn Ala Ser Met  Gly Pro Gly  Arg Thr Val

721  GTC GTTAAAGGAGAAGTGAATACA AATGCCACAAGCTTTAATGTTGACCTAGTGGCAGGA    780
      Val  Val Lys Gly Glu Val Asn Thr  Asn Ala Thr  Ser Phe Asn Val Asp Leu Val Ala  Gly

781  AGGTCAAGGGATATC GCTCTGCACTTGAACCCACGCCTGAATGTGAAAGCGTTTGTAAGA    840
      Arg  Ser Arg Asp  Ile  Ala Leu  His Leu Asn Pro Arg  Leu Asn Val Lys  Ala Phe Val Arg

841  AACTCC TTTCTTCAGGAT GCCTGGGGAGAAGAGGAGAGAAACATTACCTGCTTCCCATTT    900
      Asn Ser Phe Leu  Gln Asp Ala   Trp Gly Glu Glu Glu Arg Asn  Ile  Thr Cys Phe ProPhe

901  AGT TCTGGGATGTACTTT GAGATGATA ATT TACTGTGATGTCCGAGAGTTCAAGGTTGCA   960
      Ser  Ser  Gly Met Tyr Phe  Glu Met  Ile   Ile  Tyr Cys Asp Val  Arg  Glu Phe Lys Val  Ala

961  GTA AATGGTGTGCACAGCCTGGAGTACAAGCACAGATTTAAAGAC CTAAGCAGCATCGAC  1020
      Val Asn Gly Val  His Ser Leu  Glu Tyr Lys  His  Arg Phe Lys Asp Leu Ser Ser  Ile  Asp

1021  ACACTAGCAGTTGAT GGCGATATCCGTTTGCTGGATGTAAGGAGCTGGTAGCTATCATGA  1080
      Thr Leu Ala Val  Asp  Gly Asp  Ile  Arg Leu  Leu Asp Val  Arg  Ser Trp ***

1081  CTGCCAGAACC CTG GAAATACAAAATGGCTTATCCGATACTGGCCATGTCAAATGCATCT  1140
1141  CGC TTTCACCACAT TGTTATACTGTTAAGTTGAGCTCGCACAACATCAAGTCCTACTGGT  1200
1201  GTT GTCAGGCCTGGCCATGCAGTGTGGCTACCTCTGAATTCCCAGGA             1247
```

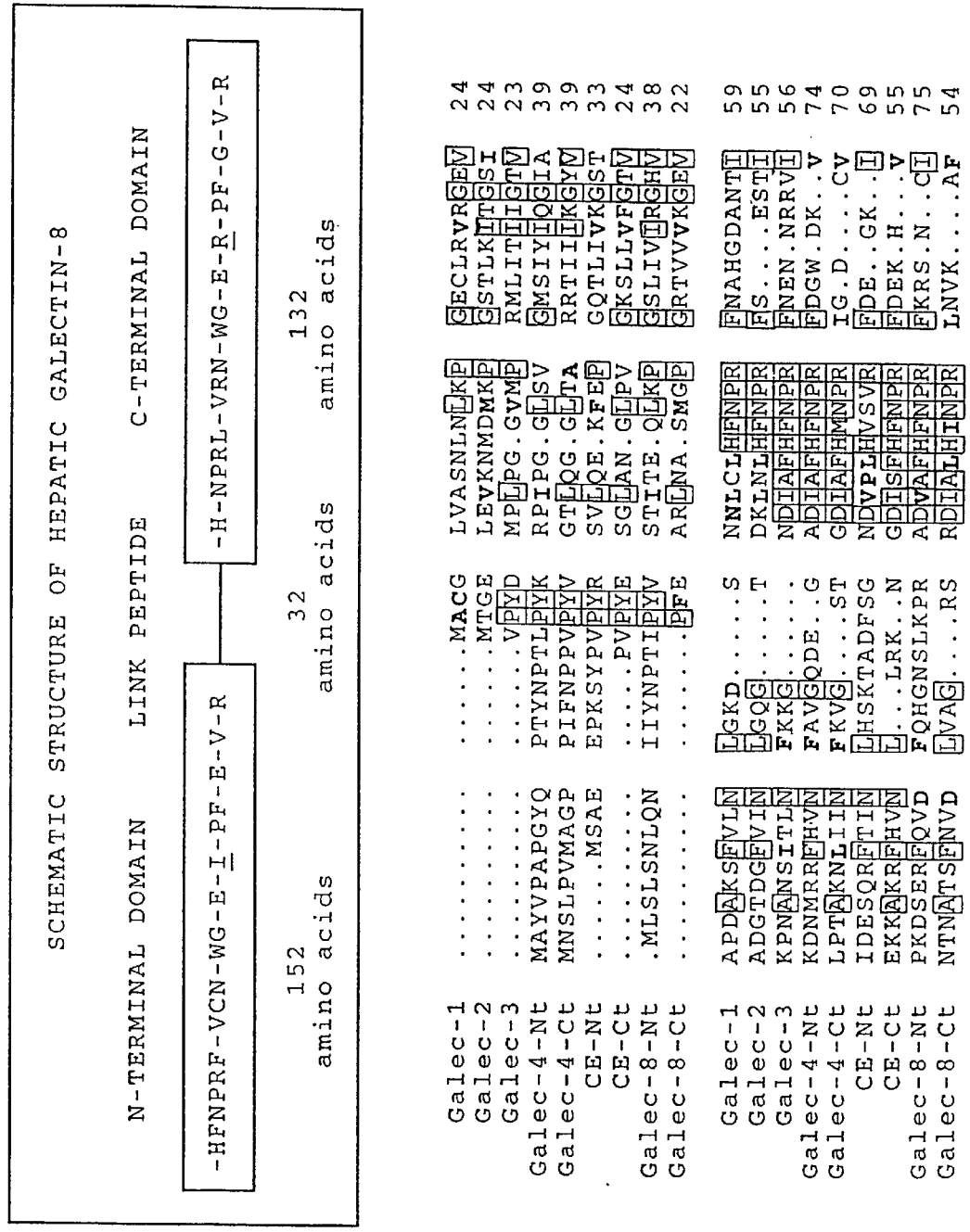

FIG. 2B

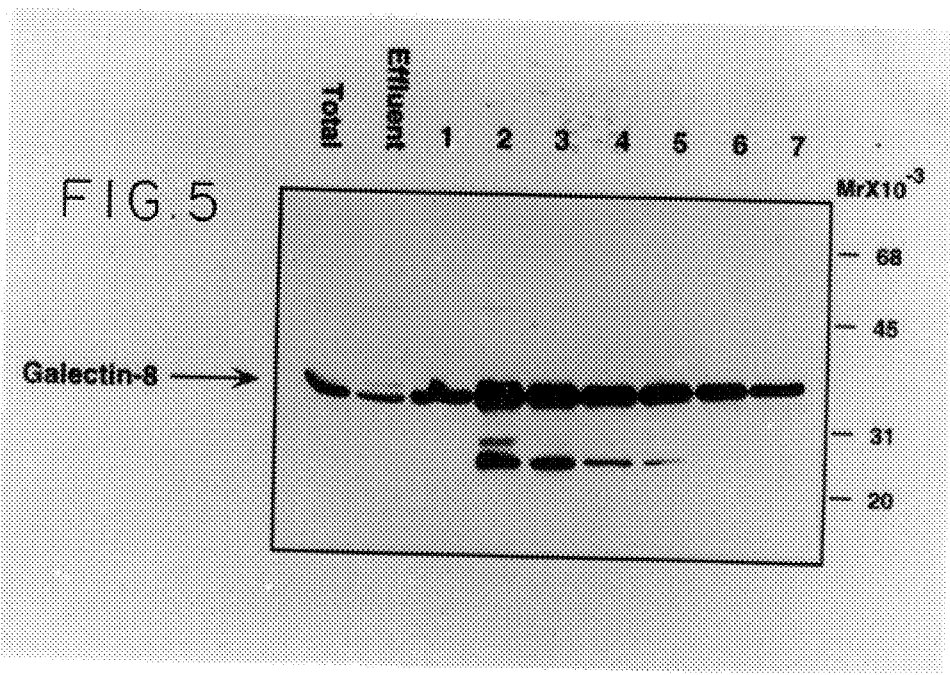
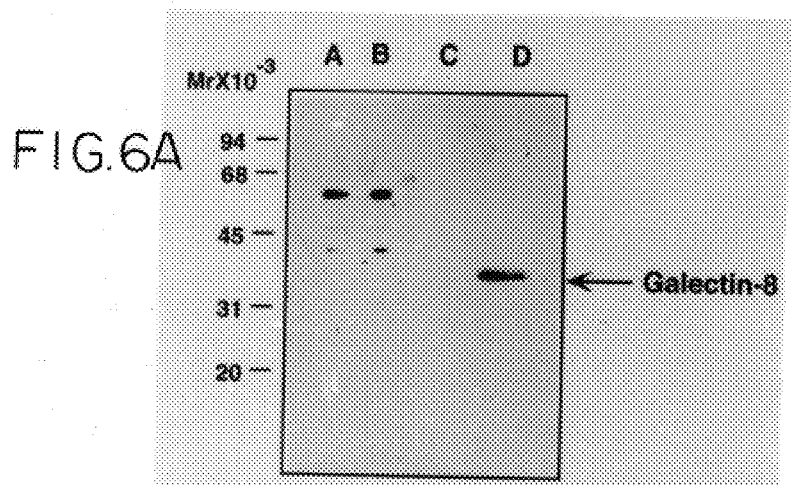
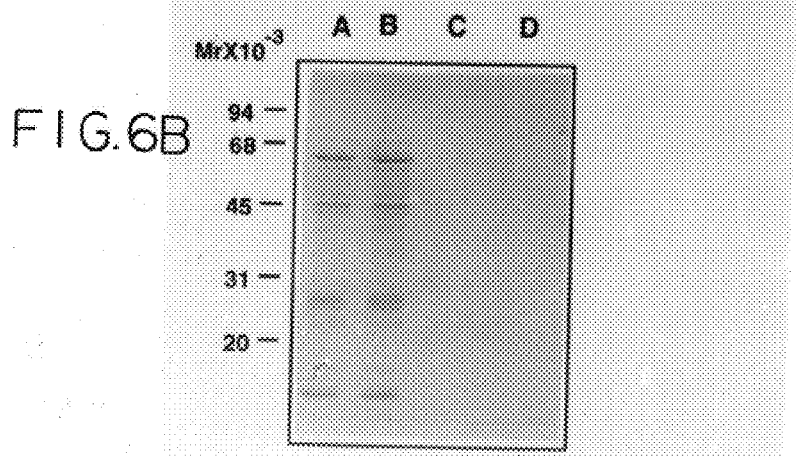

GALECTIN-8 AND GALECTIN-8-LIKE PROTEINS AND DNA MOLECULES CODING THEREFOR

FIELD OF THE INVENTION

The present invention is generally in the field of mammalian S-type lectin proteins, now designated galectins, which are thiol-dependent and specifically bind β-galactoside residues.

More specifically, the present invention relates to a new S-type mammalian lectin, termed hereinafter as "galectin-8", and to galectin-8-like proteins, to DNA molecules coding therefor and to antibodies raised against said proteins. The invention further relates to pharmaceutical compositions comprising said proteins for the purpose of cell growth regulation in general, and more particularly for inhibition of cell proliferation and for treatment of tumors.

BACKGROUND OF THE INVENTION

Lectins are involved in a wide variety of cellular functions, many of which are related to their only common feature, the ability to bind carbohydrates specifically and reversibly, and to agglutinate cells [reviewed in (1)]. Animal lectins are classified as C-lectins, which are $Ca^{2+}$-dependent and are structurally related to the asialoglycoprotein receptor, and galectins, previously known as S-type lectins, which are thiol-dependent and specifically bind β-galactoside residues. In mammals, four galectin types have been sequenced and characterized, and there is evidence for the existence of other relatives (2,3). All known members of this family lack a signal peptide, are found in the cytosol, and are isolated as soluble proteins. However, there is evidence that some members are externalized by an atypical secretory mechanism.

Galectins require fulfillment of two criteria: affinity for β-galactosides and significant sequence similarity in the carbohydrate recognition domain (CRD) (4), the relevant amino acids residues of which have been determined by X-ray crystallography (5). Galectin-1 and -2 are homodimers with subunit molecular weight of ≈14 kDa, that are not subjected to post-translational modifications (6). Galectin-1 is found in the extracellular matrix and has been shown to interact with laminin (7). The function of galectin-1 and -2 is not yet fully understood, although there is evidence that they might be involved in regulation of cell growth (8); cell adhesion (7); cell transformation (9); and embryogenesis (10).

Larger galectins (galectin-3) (previously known as CBP-35, Mac-2, RL-29) do exist ((11) and references therein). These are monomeric 29–35 kDa mosaic proteins, composed of an N-terminal half made of tandem repeats characteristic of the collagen gene superfamily, and a C-terminal half homologous to galectins-1 and -2 (11). Galectin-3 also binds laminin, and is implicated as component of growth regulatory systems; mediator of cell—cell and cell-matrix interactions; modulator of immune response; marker of neoplastic transformation, and indicator for metastatic potential of melanoma cells.

Galectin-4 was cloned from rat intestine (12), and an homologous protein was cloned from nematode (13). Galectin-4 is a monomer with molecular mass of 36 kDa. It contains tandem domains of ≈140 amino-acids each, homologous to galectin-1 and -2, that are separated by a link region (12). The function of galectin-4 is presently unknown.

Galectins may functionally substitute each other. The absence of any major phenotypic abnormalities in mice carrying a null mutation in the gene encoding galectin-1, suggests that other protein(s), presumably galectin-3, are capable of functionally substituting for galectin-1, at least at early stages of embryogenesis.

It is an object of the present invention to provide the cloning of a cDNA encoding for a novel protein that we term galectin-8. Galectin-8 has the characteristic properties of other galectins (2,3), and it is structurally related (34% identity) to rat galectin-4 (12).

SUMMARY OF THE INVENTION

According to the present invention, a novel protein of 35 Kd which has the characteristic properties of galectins (S-type mammalian lectins) was cloned from a rat liver cDNA expression library. This protein was originally called by us RL-30 protein. However, the nomenclature of S-type lectins has recently been changed to galectins (2). Since names for galectins 1–7 were already assigned (3), this new protein has now been named galectin-8, but it is to be understood that this is the same protein formerly called by us RL-30.

Thus, in one embodiment, the present invention provides a biologically active S-type lectin named galectin-8 and galectin-8-like proteins and fragments thereof selected from:

(i) the protein galectin-8 of the amino acid sequence depicted in FIG. 1 (SEQ ID NO:2);

(ii) a protein having greater than about 80 percent similarity to all or part of the sequence of amino acid residues 1–316 depicted in FIG. 1 (residues 1–316 of SEQ ID NO:2);

(iii) a protein having greater than about 80 percent similarity to all or part of the sequence of amino acid residues 1–151 depicted in FIG. 1 (residues 1–151 of SEQ ID NO:2);

(iv) a protein having greater than about 80 percent similarity to all or part of the sequence of amino acid residues 152–316 depicted in FIG. 1 (residues 152–316 of SEQ ID NO:2);

(v) a protein of (i), (ii), (iii) or (iv) in which one or more amino acid residues have been added, deleted, replaced or chemically modified without substantially affecting the biological activity of the protein;

(vi) a biologically active fragment of (i) to (v); and (vii) an homologous polypeptide to that of (i) to (vi) derived from another mammal and which has a similar biological activity to that of (i) to (vi).

In another embodiment, the present invention relates to an isolated DNA sequence encoding galectin-8 or a galectin-8-like protein.

By one embodiment, the isolated DNA sequence of the invention is one that encodes a polypeptide product of prokaryotic or eukaryotic host expression, said product having all or part of the primary structural conformation of galectin-8 or of a galectin-8-like protein and having the biological activity of galectin-8.

The above DNA sequence of the invention may be any one of the group consisting of:

(i) a DNA molecule having a nucleotide sequence derived from the coding region of a native galectin-8 or galectin-8-like gene;

(ii) a DNA molecule capable of hybridization to the cDNA clones of (i) under moderately stringent conditions and which encodes biologically active galectin-8 or a galectin-8-like protein; and (iii) a DNA molecule which differs, as a result of the degenerative nature of the genetic code, from the DNA sequences defined in (i) or (ii) and which encodes biologically active galectin-8 or a galectin-8-like protein.

By way of other embodiments, the above DNA sequence of the invention is one selected from:

(i) a DNA molecule comprising the coding nucleic acid sequence depicted in FIG. 1 (nucleotides 121–1068 of SEQ ID NO:1);

(ii) a DNA molecule having the nucleic acid sequence of (i) in which one or more codons has been added, replaced or deleted in a manner that the polypeptide encoded by said sequence essentially retains the same biological properties as the polypeptide encoded by an unaltered DNA sequence;

(iii) a DNA molecule encoding a polypeptide having an amino acid sequence of a polypeptide encoded by the DNA molecule of (i) or (ii) but which differs therefrom in view of the degenerative nature of the genetic code;

(iv) a DNA molecule having a coding nucleotide sequence, which is homologous to the DNA molecule of (i), (ii) or (iii), which is derived from a mammal other than rats and which encodes a polypeptide having a similar biological activity to that encoded by the sequences of (i), (ii) or (iii);

(v) a fragment of the coding sequence of (i)–(iv) which encodes a polypeptide which essentially retains the biological properties of the polypeptide encoded by the unfragmented DNA molecule; and (vi) a DNA molecule comprising the coding DNA sequence of a fragment of (i)–(v) and additional DNA sequences in the 3' and 5' ends.

In a further embodiment, the present invention relates to a recombinant DNA molecule comprising a coding sequence according to any of (i)–(iii) and (i)–(iv) above or a fragment thereof according to (v) or (vi) above.

The present invention also provides a recombinant expression vector comprising any one of the above-mentioned DNA molecules of the invention. Such a recombinant expression vector may be one capable of being expressed in prokaryotic or eukaryotic hosts, the vector containing, in addition to any one of the above galectin-8 or galectin-8-like protein encoding sequences, various other sequences such as, for example, those sequences that are known to be important for expression of the desired sequence and the maintenance and propagation of the vector in the host cell. Construction of such recombinant expression vectors is by way of any of the known procedures.

The present invention further provides a method for preparing galectin-8 or a galectin-8-like protein or a biologically active fragment thereof, comprising culturing a suitable host cell containing the above recombinant vector of the invention under conditions promoting expression.

The protein of the invention may be prepared, as noted above, by expression of a recombinant vector comprising a DNA sequence encoding the protein, or it may be isolated and purified from various mammalian tissues using standard procedures for protein extraction and purification. In such purification procedures there may be employed yet another aspect of the present invention, namely, antibodies which are immunoreactive with native or recombinant galectin-8 or with a galectin-8-like protein. Such antibodies may be applied in standard affinity chromatography methods to provide for the final purification steps of the galectin from various tissues. The preparation of the antibodies is by standard procedures using native or recombinant galectin-8 or a fragment thereof or a galectin-8-like protein or a fragment thereof as antigen or immunogen to stimulate antibody production in suitable animals. Both polyclonal and monoclonal antibodies to galectin-8 are encompassed by the invention. These antibodies can be prepared by standard procedures well-known in the art.

The anti-galectin-8 antibodies of the invention may also be employed in an assay method for the detection of overexpression of galectin-8 in mammalian tissue, said method comprising applying an effective amount of the antibodies to a tissue or body fluid sample obtained from a mammal and determining the extent of antibody binding to the sample. In such an assay, standard procedures may be employed, such as, for example, ELISA assay procedures.

In addition, the present invention also provides pharmaceutical compositions comprising as active ingredient an effective amount of galectin-8 or of a mammalian galectin-8-like protein and a suitable diluent or carrier, in particular compositions for cell growth regulation, more specifically for the inhibition of cell proliferation, for example for the treatment of cancer.

In these above compositions the diluents or carriers may be any of those substances well known in the art for the preparation of pharmaceutical compositions, and likewise the compositions may be prepared by standard procedures. Actual dosages and modes of administration of the above compositions are to be determined by skilled professionals.

DESCRIPTION OF THE DRAWINGS

FIG. 1 depicts the cDNA sequence (SEQ ID NO:1) of galectin-8 and deduced protein sequence (SEQ ID NO:2). The cDNA sequence of 1247 base pairs (bp) contains an open reading frame from 121–1068 bp, which encodes for a protein of 316 amino acids.

FIGS. 2A–2B show that galectin-8 encodes for a galectin with two homologous carbohydrate-binding regions. A schematic structure of galectin-8 is presented (top). Each box represents a putative carbohydrate-binding domain, linked by a 32 amino acid long peptide. Shown are invariant amino acids preserved in most galectins analyzed so far, e.g. SEQ ID NO:19 in the boxed N-terminal carbohydrate-binding domain. The Arg residue, indispensable for sugar binding, located at the C-terminal carbohydrate recognition domain (CRD), and its corresponding Ile residue, localized to the N-terminal CRD, are underlined. Amino acid sequences of different galectins are presented for comparison (bottom). These include: human galectin-1 (Galec-1) (SEQ ID NO:3); human galectin-2 (Galec-2) (SEQ ID NO:4); the carbohydrate binding domain (amino acids 128–263) of rat galectin-3 (Galec-3) (SEQ ID NO:5); N-terminal (Galec-4-Nt) (SEQ ID NO:6) and C-terminal (Galec-4-Ct) (SEQ ID NO:7) halves of galectin-4; N-terminal (CE-Nt) (SEQ ID NO:8) and C-terminal (CE-Ct) (SEQ ID NO:9) halves of a 32-kDa β-galactoside-binding protein from *Caenorhabditis elegans*; N-terminal (Galec-8-Nt) (SEQ ID NO:10) and C-terminal (Galec-8-Ct) (SEQ ID NO:11) halves of galectin-8. Residues with shared identity are boxed. Residues with shared similarity are shaded.

FIG. 5 shows binding of tag-free recombinant galectin-8 (r-galectin-8) to lactosyl-Sepharose. Tag-free r-galectin-8 was expressed in pLysS as described under "Experimental Procedures". After centrifugation, 30 ml of the soluble bacterial proteins were purified over 5 ml of lactosyl-Sepharose. r-galectin-8 was eluted with 100 mM lactose in buffer-I, and 1 ml fractions were collected. Ten μl of the total and effluent fractions and 50 μl from each elution fraction were resolved by 12% SDS-PAGE, transferred to nitrocellulose and Western immunoblotted with lp-lec8 antibodies.

FIGS. 6A and 6B show binding of rat hepatic galectin-8 to lactosyl-Sepharose. Five g of rat liver were homogenized in buffer-I as described under "Experimental Procedures" and cytosolic extracts (25 ml) were applied over 5 ml of lactosyl-Sepharose. After extensive washing the bound proteins were eluted with 100 mM lactose in buffer-I. One ml fractions (numbered 1–10) were collected and frozen for a period of 16 h at −20° C. Eluted fractions (N° 3–5) were toughed, centrifuged for 15 min at 12000×g and the pellets were resuspended in 50 ml sample buffer (34) . Ten μg protein of total (A) and effluent (B) fractions as well as 50 μl of the supernatant (C) and resuspended pellet (D) of the eluted fractions (N° 3–5) were resolved by 12% SDS-PAGE, transferred to nitrocellulose and Western immunoblotted with lp-lec8 antibodies (FIG. 6A), or subjected to Coomasie staining (FIG. 6B).

DETAILED DESCRIPTION OF THE INVENTION

Galectin-8 is a novel, widely expressed protein of 35 kDa which has the characteristic properties of galectins (S-type mammalian lectins). Three lines of evidence demonstrate that galectin-8 is indeed a novel galectin: i. its deduced amino acid sequence contains two domains with conserved motifs that are implicated in the carbohydrate binding of galectins; ii. in vitro translation products of galectin-8 cDNA or bacterially-expressed recombinant galectin-8 are biologically active and possess sugar-binding and hemagglutination activity; iii. a protein of the expected size (34 kDa), that binds to lactosyl-Sepharose and reacts with galectin-8-specific antibodies is present in rat liver and comprises 0.025% of the total Triton-soluble hepatic proteins.

Overall, galectin-8 is structurally related (34% identity) to galectin-4, a soluble rat galectin with two carbohydrate-binding domains in the same polypeptide chain, joined by a link peptide. Nonetheless, several important features distinguish these two galectins: i. Northern blot analysis revealed that unlike galectin-4 that is confined to the intestine and stomach, galectin-8 is expressed in liver, kidney, cardiac muscle, lung, and brain; ii. unlike galectin-4, but similar to galectins-1 and -2, galectin-8 contains 4 Cys residues; iii. the link peptide of galectin-8 is unique and bears no similarity to any known protein; iv. the N-terminal carbohydrate-binding region (CRD) of galectin-8 contains a unique WG-E-I motif instead of the consensus WG-E-R/K motif implicated as playing an essential role in sugar-binding of all galectins. Together with galectin-4, galectin-8 therefore represents a subfamily of galectins consisting of a tandem repeat of structurally different CRDs within a single polypeptide chain.

As used herein, the term "galectin-8-like protein" refers to a protein derived from any mammal, including humans, which protein presents homology to galectin-8 as defined in the present invention and has the biological properties of galectin-8.

Galectin-8 was cloned when a λ-ZAP rat liver cDNA library was screened with affinity-purified antibodies directed against a 14-amino acid peptide located at the C-terminal end of the insulin-receptor substrate 1 (IRS-1) (14). Since galectin-8 bears no sequence similarity either to IRS-1, or to the peptide used as immunogen, it was suspected that the reactivity towards IRS-1 antibodies could be due to a false positive reaction. This conclusion is supported by the fact that the anti-peptide antibodies used for screening, failed to react with purified recombinant galectin-8 either by means of immunoprecipitation, or immunoblotting.

Figure 8:
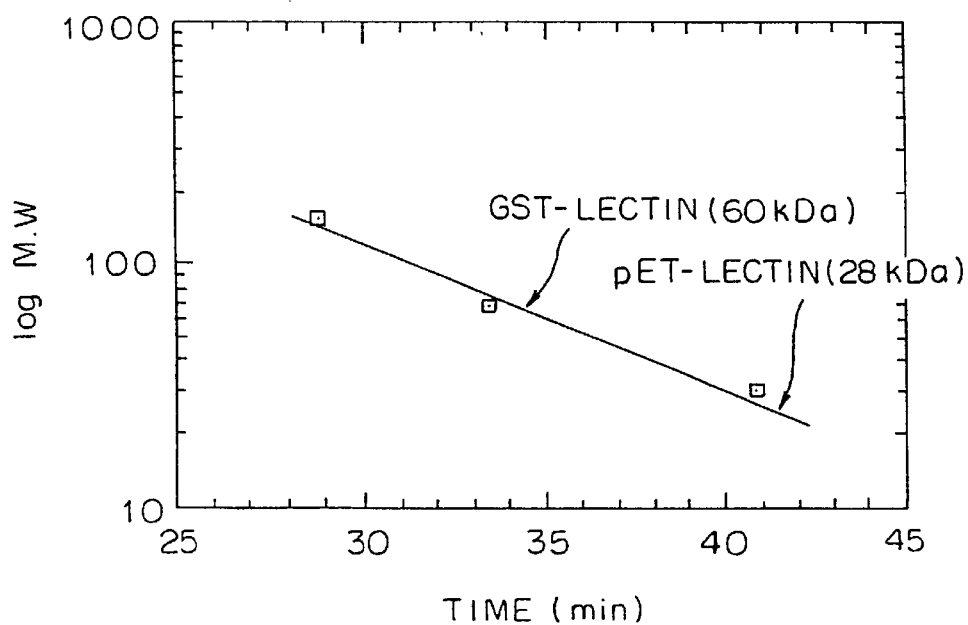
FIG. 8 shows chromatography of galectin-8 over a FPLC column. Approximately 100 μg protein was loaded onto Superdex-200 HR (Pharmacia) FPLC column equilibrated with buffer A (PBS, 4 mM β-mercaptoethanol, 2 mM EDTA), and run for 60 min at 0.5 ml/min. O.D. was measured at 215 nm, and the column profile was obtained by running separately standard marks.

The primary structure of galectin-8 resembles that of galectin-4, namely, two homologous (38% identity) carbohydrate-binding regions (CRDs) linked by a short ≈30-amino acids linking peptide. This unique architecture is shared so far only by two galectins: rat galectin-4 (12) and its *C. elegans* homologue (13). Other galectin types, that contain a single CRD, exist and function as non-covalent dimers, which provides them with the potential to aggregate or agglutinate glycoconjugates. Since galectin-4 exists as a monomer, experiments were carried out to determine whether galectin-8 exists as a monomer or a dimer. Separation of galectin-8 over Superdex-200 HR (Pharmacia) FPLC column according to the present invention revealed that galectin-8 exists as a monomer (FIG. 8). Hepatic galectin-8 (FIG. 6) has a similar mobility on SDS-PAGE as its recombinant counterpart (FIG. 5). This suggests, though not proves, that hepatic galectin-8 is neither heavily glycosylated, nor it is subjected to extensive post-translational modifications (e. g. phosphorylation).

Although galectin-8 contains two putative CRDs, potential differences in sugar-binding between the domains is predicted from a critical difference in their sequence [WG-E-I vs. WG-E-R at the N- and C-terminal CRDs of galectin-8, respectively (cf. FIG. 2)]. The (underlined) Arg residue has been implicated as playing an important role in the interactions between galectins and the glucose moiety of lactose (5). Furthermore, site-directed mutagenesis studies (4) indicate that this conserved Arg is indispensable for sugar binding. The presence of Ile$^{90}$ (instead of an Arg) at the N-terminal CRD of galectin-8 suggests that this domain might have a different sugar-binding specificity. In that respect galectin-8 resembles galectin-4 whose CRDs are distinct both in structure and sugar-binding specificity (12). The presence of two CRDs with a potentially different sugar-binding specificity might be required to achieve high affinity binding to multivalent glycoprotein ligands possessing different sugar moieties.

Like other galectins, galectin-8 lacks a classical signal sequence or a transmembrane segment. Indeed, galectin-8 was isolated from the cytosolic fraction of rat liver. These findings do not exclude the possibility that galectin-8, like other galectins, could be externalized by an atypical secretory mechanism (15). Immunohistochemical studies revealed that secreted galectins are concentrated in evaginations of the plasma membrane, which pinch off to form labile lectin-rich extracellular vesicles which may interact with cell surface proteins (15). Expression of galectin-8 seems to be developmentally regulated. Very low levels of expression were noted in whole embryos, while high levels of expression were noted in adult tissues. In that respect galectin-8 might resemble other galectins that were implicated as regulators of cell growth and embryogenesis (8–10).

The invention will now be described by way of the following non-limiting examples and the accompanying drawings.

EXAMPLES

Experimental Procedures (a) Materials—Restriction enzymes were purchased from Fermentas. Radiolabeled nucleotides and [$^{35}$S]methionine were from Amersham (Amersham, Buckinghamshire, UK). All other reagents were from Sigma unless stated otherwise.

(b) Antibodies—Antisera to insulin receptor substrate 1 (anti-IRS-1) were raised in rabbits according to standard procedures, by injection of a peptide Cys-Tyr-Ala-Ser-Ile-Asn-Phe-Gln-Lys-Gln-Pro-Glu-Asp-Arg-Gln (SEQ ID NO:12) corresponding to the carboxy-terminal 14 amino acids of rat liver IRS-1 (and an additional Cys residue at the N-terminal site). Antibodies were affinity-purified from the serum by adsorption onto a column of peptide coupled to Affi-gel 10, elution with 100 mM HCl glycine pH 2.7, and immediate neutralization. Anti glutathione-S-transferase (GST) antisera was a kind gift from Y. Yarden (Weizmann Institute).

(c) Screening of Rat Liver cDNA Expression Library—λ-Zap rat liver cDNA library in the Lambda ZAP II Vector (Stratagene, La Jolla, Calif.), was screened separately and in duplicate with affinity-purified anti IRS-1 antibodies (see (b) above). Screening was carried out according to the instruction manual provided by the manufacturer (picoBlue™ Immunoscreening Kit, Stratagene, La Jolla, Calif.). Positive plaques were isolated by three repetitive cycles of the procedure. The ExAssist/SOLR system (Stratagene, La Jolla, Calif.) was used to allow efficient excision of the Bluescript phagemid from the λ-ZAP vector, and SOLR cells containing positive clones were isolated. Initial DNA sequencing of one positive clone was carried on both strands, using T3 and T7 universal primers with Sequenase version 2.0, (United States Biochemicals, Cleveland, Ohio). Subsequent sequencing was carried out with internal primers designed as the sequencing progressed. All other manipulations of nucleic acids such as restriction, ligations, transformation, gel electrophoresis, blotting, gel elution, radiolabeling, and preparation of buffers were done using standard protocols (16). Search of the GenBank revealed that the isolated clone is unique and it bears no sequence similarity with IRS-1, or the peptide, against which the antibodies were raised. The reason why this clone was picked up by the antibodies remains unclear.

(d) Northern Blot Analysis—RNA extraction was carried out as described (16). Total RNA (30 μg) was electrophoresed, the gel was blotted onto nitrocellulose, and the blot was probed with labeled PCR product which was obtained by the following procedure. Two primers, 5'-CCCGACAATCCCCTATGTCAGTACC-3' (SEQ ID NO:13) and 5'-GCATGGCCAGGCCTGACAACA-3' (SEQ ID NO:14), were used to amplify the entire cDNA coding sequence of galectin-8, using the cloned cDNA in Bluescript as a template. The PCR products were labeled with [α-$^{32}$P]-ATP by random priming with DECAprime II DNA labeling kit (Ambion, Austin, Tex.). Hybridization was carried out at 42° C. in 50% formamide 5×SSC, and washes were at 60° C. in 0.1×SSC, 0.1% SDS.

(e) Expression of recombinant galectin-8 in *Escherichia Coli*—Expression of galectin-8 as a GST fusion protein (GST-galectin-8) was carried out by using two primers: T7 and 5'-GGGGGGGGATCCATGTTGTCCTTAAGCAAT-3' (SEQ ID NO:15) (the EcoR I, Nde I, and BamH I restriction sites, respectively, in the primer are underlined) to amplify the entire cDNA insert of galectin-8, using the cloned cDNA in Bluescript as a template. The PCR products were digested with BamH I and EcoR I, gel-purified, and ligated into pGeX-2X expression plasmid (Pharmacia) in the TOP$_{10}$ bacterial host (Invitrogen). For direct expression of (tag-free) r-galectin-8, a sense primer 5'-GGGGGGCATATGTTGTCCTTAAGCAAT-3' (SEQ ID NO:16) and an antisense primer 5'-GGGGGGGGATCCGCCATTTTGTATTTCCAG-3' (SEQ ID NO:17) were used to amplify the entire coding sequence of galectin-8, using the cloned cDNA in Bluescript as a template. The PCR products were digested by Nde I and BamH I, gel-purified, and ligated into a pET-3a expression plasmid (Novagen) in the pLysS bacterial host. Sequencing of both expression plasmids was carried out to ensure proper, in-frame, ligation of the inserts.

To express GST-galectin-8, bacteria were cultured in 0.5 liter of LB medium until the absorbance at 600 nm was 0.5. Expression of GST-galectin-8 was then induced with 5 mM isopropyl-1-thio-β-D-galactopyranoside (IPTG) for 4 h. To isolate the recombinant protein, a bacterial pellet was isolated by centrifugation, resuspended in 30 ml of buffer I (phosphate buffered saline containing 4 mM β-mercaptoethanol, 2 mM EDTA, 10 μg/ml soybean trypsin inhibitor, 2 mM benzamidine and 1 mM phenylmethylsulfonyl fluoride, pH 7.5), and lysed by sonication. Debris were removed by centrifugation at 38,000×g at 4° C. for 45 min., and 30 ml of the soluble extract were passed over 5 ml of lactosyl-Sepharose. Unbound proteins were eluted with buffer I, while the lectin was subsequently eluted with buffer I containing 100 mM lactose. A similar procedure was utilized to express r-galectin-8 in the pET-3a expression plasmid, save for the fact that the bacteria were centrifuged when the absorbance at 600 nm was 0.3, without addition of IPTG. Recombinant galectin-8 was isolated under reducing conditions, since in their absence the protein underwent denaturation even when maintained at 4° C.

(f) In-Vitro translation of galectin-8—For in vitro translation of galectin-8, the BamH I/EcoR I-digested PCR product, described above, was cloned into pcDNA I mammalian expression plasmid (Invitrogen). In vitro translation in the presence of [$^{35}$S]-methionine was performed using the TNT in vitro translation kit (Promega) according to the manufacturer's instructions.

(g) Immunoprecipitation—lp-lec8 antibodies were added to 60 µl of 50% protein A-Sepharose in 0.1 M Tris buffer, pH 8.5, and were incubated for 1 hr at 4° C. Bacterial cell extracts were prepared in buffer I. 500 µl extracts (0.8 mg) were incubated for 2 hr with the antibody-protein A-Sepharose complex. Immunocomplexes were washed, suspended in sample buffer, resolved on 10–12% SDS-PAGE and transferred to nitrocellulose for Western blotting.

(h) Protein electrophoresis and blotting—Immunoblotting was carried out by standard procedures. The blotted proteins were incubated with lp-lec8 antibodies at 4° C. for 16 h and then were extensively washed. To detect antibody binding, a horseradish peroxidase-conjugated Protein A ECL kit (Amersham) was used according to the manufacturer's instructions.

(i) Purification of galectin-8 from rat liver—Freshly isolated rat livers from male Wistar rats were homogenized in buffer I (1 g/5 ml) supplemented with 10 µg/ml aprotinin and 5 µg/ml leupeptin. The homogenate was centrifuged for 1 h at 4° C. at 100,000×g, and 25 ml of the supernatant were passed over 5 ml of lactosyl-Sepharose, following the procedure described above. The eluted fractions were kept frozen at −20° C. Since intact galectin-8 denatures upon freezing, the frozen fractions were toughed, and centrifuged at 12,000×g, for 15 min. at 4° C. to precipitate, and thus concentrate, galectin-8. Supernatants and pellets were resuspended in sample buffer, resolved by 12% SDS-PAGE, transferred to nitrocellulose and Western immunoblotted with lp-lec8 antibodies. The amount of galectin-8 in rat liver was estimated using 100,000×g supernatants that were prepared in buffer I in the presence of 1% Triton-X-100.

(j) Assay of lectin activity—The biological activity of galectin-8 was assayed by measuring its ability to agglutinate formaldehyde-fixed, trypsin-treated rabbit erythrocyte. Rabbit erythrocytes were trypsin-treated according to Lis and Sharon (17). Cells were incubated for 1 h at 37° C. with 0.1% trypsin in PBS, washed five times in 10 volumes of 0.9% NaCl/packed ml of cells, and resuspended in 0.9% NaCl to yield an erythrocyte suspension with an absorbance of 1.5 at 620 nm. Half ml aliquots of erythrocyte suspension was incubated for 45 in at room temperature with the lectin solution. Aliquots (0.2 ml) of the upper part of the tube were removed, mixed with 0.8 ml of PBS, and the optical density at 620 nm was monitored.

EXAMPLE 1

Isolation of galectin-8, a novel mammalian galectin

A cDNA encoding for a new galectin, termed galectin-8, was cloned from a λ2-Zap rat liver cDNA library (FIG. 1). The isolated clone contained an open reading frame (ORF) (nucleotides 112–1068) with a potential initiation ATG codon at position 121. This ORF coded for 316 amino acids, which form a protein of about 35 kDa. The putative coding sequence was followed by a signal for translation termination (TAG) and 176 nucleotides of 3'-untranslated region. Search of the GenBank for similar nucleotide sequences revealed that this sequence is unique. This sequence, depicted in FIG. 1, has been submitted to the Gen Bank™/EMBL Data Bank with accession number U09824.

Figure 2B:
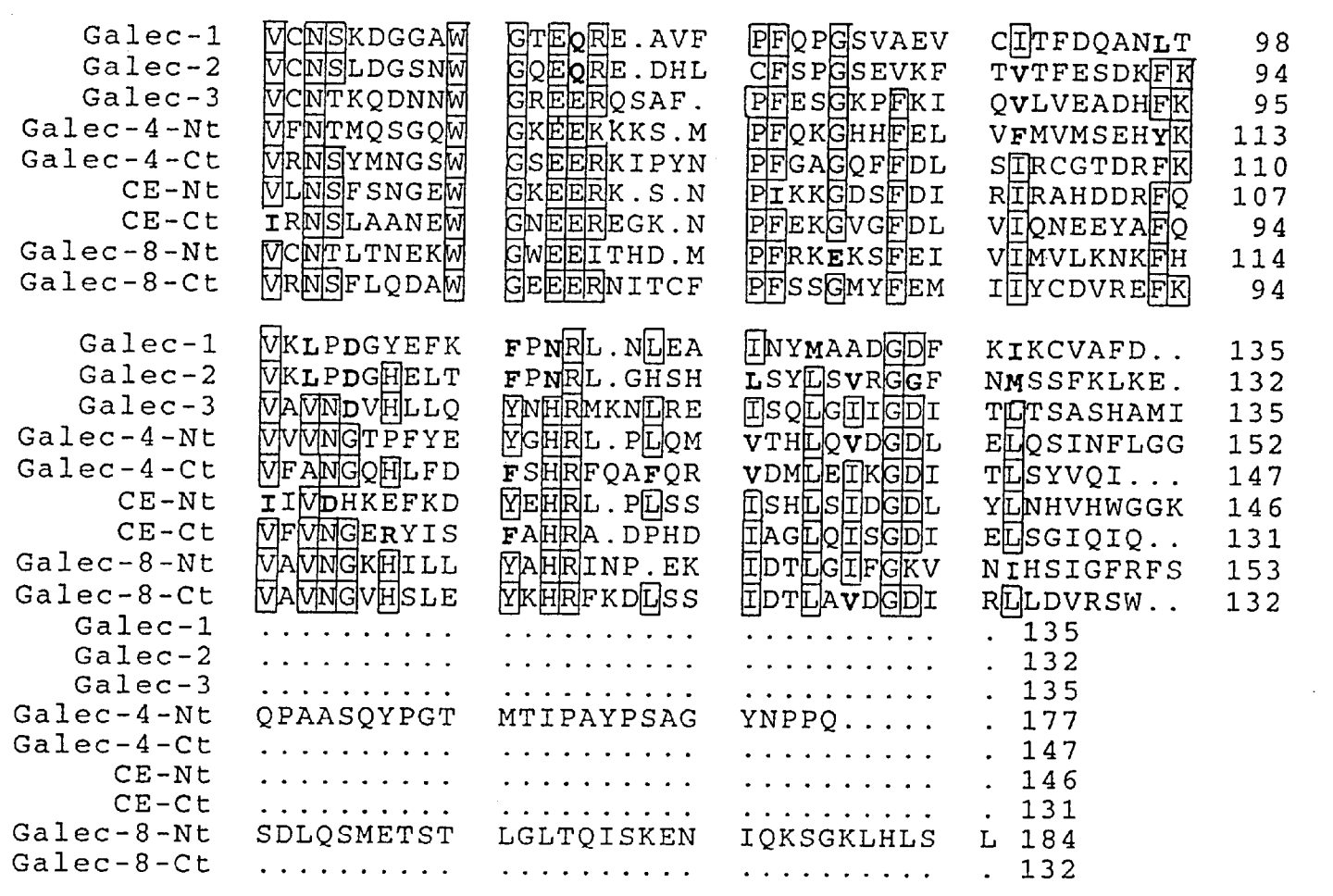

Analysis of galectin-8 using alignment algorithms suggested the presence of two homologous domains ≈140 amino acids each, linked by a link peptide of 32 amino acid residues (FIG. 2, top). Thirty eight percent of the amino acids were identical between the first and second domains (FIG. 2, bottom). Both domains contained sequence motifs (e. g. H-NPR; WG-EE) that have been conserved among most carbohydrate recognition domains (CRDS) of galectins analyzed so far. Structurally, galectin-8 resembles a 32-kDa β-galactoside-binding protein from *Caenorhabditis elegans* (13) (CE-galectin), and rat galectin-4 (galectin-4) (12), that also contain two CRDs connected by a link peptide (FIG. 2). At the level of nucleic acids, galectin-8 is 50% and 45% homologous to galectin-4 and CE-galectin, respectively. At the level of amino acids, galectin-8 shares 34% and 31% identity, respectively, with the above proteins. No homology with any known protein was found in the region of the link peptide. Like other galectins, galectin-8 lacks classical signal sequence or transmembrane segment, but it contains three potential N-linked glycosylation (Asn-X-Ser/Thr) sites. Analysis of its predicted secondary structure (not shown), revealed that the N-and C-terminal domains of galectin-8 share a great degree of structural homology, as expected from their primary structure. Both domains are predicted to form several β-sheets, a structural feature of other galectins (5).

The cDNA clone encoding galectin-8 may be used as a probe to isolate and characterize the full length genomic sequence encoding this protein in various mammals, for example, humans and rats, using standard procedures.

Further, the above mentioned cDNA clone and/or the full-length genomic sequence encoding galectin-8 may be used to generate, by standard procedures, fragments containing only a portion of the full-length galectin-8 sequence, where each fragment essentially retains at least one of the biological activities of galectin-8. These fragments are termed 'biologically active fragments'. Moreover the galectin-8 sequence may also be used to generate analogs of galectin-8 (herein termed "galectin-8-like proteins") or fragments thereof, such analogs having at least one amino acid residue added, deleted or replaced by another in comparison to the native galectin-8 sequence, and such analogs essentially retaining the biological activity of their non-modified progenitor molecules.

EXAMPLE 2

Antibodies against the link peptide of galectin-8 (lp-lec8) or against recombinant galectin-8 (rgalectin-8)

Since galectin-8 contains a unique link peptide region, antibodies against this region are not expected to cross-react with other galectins. A peptide corresponding to positions 168–182 in the link peptide of galectin-8 (and an additional Cys residue at the N-terminal site) of the sequence Cys-Gln-Ile-Ser-Lys-Glu-Thr-Ile-Gln-Lys-Ser-Gly-Lys-Leu-His-Leu (SEQ ID NO:18) was synthesized, purified, and polyclonal antibodies against it were raised in rabbits by standard procedures. The antibodies (denoted lp-lec8) were affinity-purified over a column of immobilized peptide. lp-lec8 antibodies reacted specifically with galectin-8 both by means of immunoprecipitation (IP) and immunoblotting (IB) . Furthermore, these interactions could be specifically blocked in the presence of 1 µM peptide (not shown). Since lp-lec8 antibodies specifically react with the link peptide of galectin-8, antibodies towards whole recombinant galectin-8 were generated as well. Purified tag-free rgalectin-8 was used as immunogen for injection into rabbits, and antibodies were affinity purified over columns of Protein A coupled to agarose. These antibodies reacted specifically with galectin-8 both by means of immunoprecipitation and immunoblotting.

These antibodies are most useful for identification of naturally occurring degradation products of galectin-8, where the link peptide region has been deleted, or proteins homologous to galectin-8 in domains different from the link peptide region. Cross-reactivity with homologous proteins is assessed by the ability of lp-lec8 antibodies to react with the suspected candidates, and by the ability of peptides, directed against unique regions of galectin-8, outside the link peptide region, to compete with galectin-8 antibody binding.

EXAMPLE 3
In-vitro-translated galectin-8 is biologically active

Figure 4:
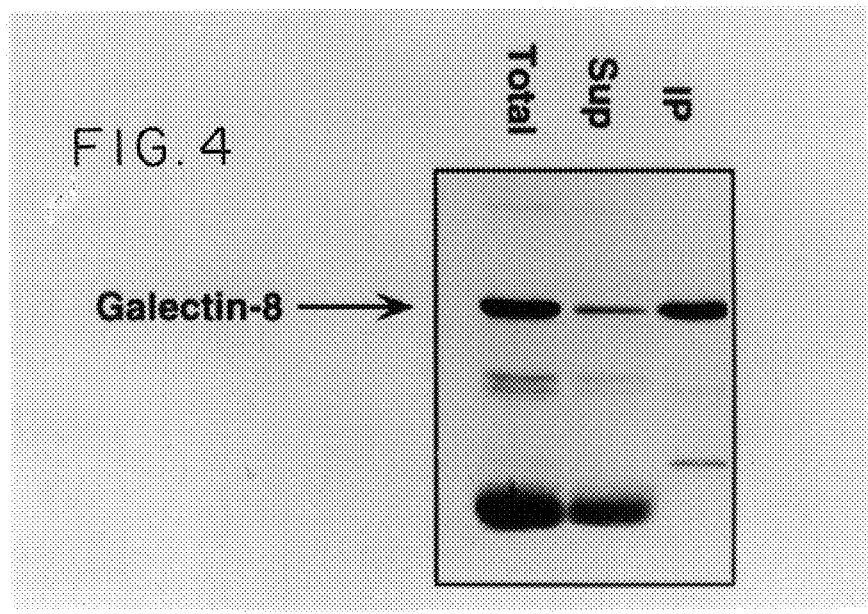
FIG. 4 shows immunoprecipitation of in-vitro translation product of galectin-8 by lp-lec8 antibodies. Fifty μl of the $^{35}$S-labeled galectin-8, expressed as in-vitro translation product (see "Experimental Procedures"), were immunoprecipitated by lp-lec8 antibodies as described in Example 2 herein. Five μl of the total $^{35}$S-labeled galectin-8 (total), 5 μl of the fraction not precipitated by the antibodies (Sup), and 50 μl of the immunoprecipitated fraction (IP) were subjected to 12% SDS-PAGE and autoradiography.

Galectin-8 cDNA was transcribed and translated in vitro using a TNT (Promega) kit. An $^{35}$S-labeled product of the expected size (34 kDa) was synthesized (FIG. 4). This in vitro-translated product was indeed galectin-8 since it could be immunoprecipitated with lp-lec8 antibodies described in Example 2 (FIG. 4). As predicted by its primary amino acid sequence, in vitro-translated galectin-8 exhibited the key feature of galectins, namely, capacity to bind to a column of lactosyl-Sepharose in the presence of reducing agents, and to be eluted with 0.1 M lactose (not shown).

EXAMPLE 4
Recombinant galectin-8, expressed in bacteria, remains soluble and retains lectin biological activity To further characterize galectin-8, it was expressed in bacteria as a GST-fusion protein. GST-galectin-8 remained bound to glutathione-Sepharose beads, and could be eluted with glutathione (not shown). GST-galectin-8 retained its sugar-binding capacity and could be purified by binding to lactosyl-Sepharose and elution with 0.1 M lactose (not shown). Routinely, 3 mg GST-galectin-8 could be purified in such a way from 1 liter of bacterial extracts. Like other galectins, GST-galectin-8 also maintained hemagglutination activity. Half and maximal activities were obtained with 0.1 and 1 $\mu$g/ml of GST-galectin-8, respectively.

In a different approach a tag-free rgalectin-8 was expressed employing a pET-3a expression plasmid (Novagen) in the pLysS bacterial host. Unlike intestinal recombinant galectin-4 that precipitates and cannot be extracted with buffers that preserve its lectin activity (12), rgalectin-8 could be readily extracted from bacteria in a soluble form rgalectin-8 was not subjected to major proteolytic cleavage, as it migrated at the expected size of 34 kDa. Most important, rgalectin-8 retained its sugar-binding activity and 1.2 mg protein/liter bacteria were obtained following its purification over lactosyl-Sepharose column (FIG. 5).

To optimize expression, the induction time and the concentration of IPTG is varied. To further purify GST-galectin-8 or rgalectin-8, approximately 5 mg protein are loaded onto a column of antibodies covalently linked to Affi-Gel 15 beads (Pharmacia). The bound proteins are then eluted with HCl/glycine buffer (pH 2.8) and immediatly neutralized.

EXAMPLE 5
Endogenous galectin-8 is present in rat liver

To demonstrate the presence of endogenous galectin-8 in rat liver, a cytosolic (100,000×g supernatant) liver extract was prepared, applied to a column of lactosyl-Sepharose, and proteins retained specifically by the column were eluted with 0.1 M lactose. Advantage was taken of the fact that hepatic galectin-8 denatures and precipitates upon freezing. Fractions, eluted from the lactosyl-Sepharose column, were therefore frozen at −20° C., thawed, and centrifuged to precipitate, and thus concentrate, the hepatic galectin-8. Staining with Coomasie Blue revealed that most hepatic proteins failed to interact with lactosyl-Sepharose and therefore remained in the flow-through fraction (FIG. 6A). Immunoblotting with lp-lec8 antibodies (FIG. 6B) revealed that while hepatic galectin-8 could not be detected in total cytosolic liver extracts, a 36 kDa protein, with the expected size of galectin-8, remained bound to, and could be eluted from the lactosyl-Sepharose column. Hepatic galectin-8 was readily detected in the pellets, but not in the supernatants of the (frozen and thawed) eluted fractions, indicating that indeed it denatures upon freezing. These results suggest that functionally active cytosolic galectin-8 is present in rat liver (FIG. 6).

To estimate the amounts of galectin-8 in rat liver, Triton-soluble liver extracts were prepared, and resolved by means of SDS-PAGE. Known amounts of rgalectin-8 were run in parallel. All samples were then subjected to Western immunoblotting, using anti-rgalectin-8 antibodies. Assuming that the immunoreactivity of rgalectin-8 and the endogenous hepatic protein are comparable, we calculated that ~25 ng of galectin-8 are present in 100 mg of Triton-soluble liver extracts. These findings suggest that galectin-8 comprises ~0.025% of total Triton-soluble hepatic proteins.

EXAMPLE 6
Galectin-8 is widely expressed. Tissue distribution and cellular localization of galectin-8.

Identifying tissues where galectin-8 is highly expressed provides important clues related to its possible function and involvement in development. More important, determining whether galectin-8, like other galectins, is externalized, is of fundamental importance in attempts to assess its mode of action. Three different approaches may be used to gain a detailed tissue distribution of galectin-8. i. Northern blot analysis of rat tissues; ii. to ascertain that the level of mRNA indeed reflects the level of expression of galectin-8, the abundance of galectin-8 in various tissues may be determined by Western blot analysis using anti-rgalectin-8 antibodies. Since galectin-8, like other galectins, is prone to proteolysis, freshly isolated tissues are directly homogenized in 4M guanidinium-HCl to inactivate all proteases. The amount of galectin-8 in the tissue under study is determined following SDS-PAGE, Western blotting, and probing with anti-rgalectin-8 antibodies. iii. In addition, tissues of interest (e. g. liver and brain) will be studied in more detail by in-situ hybridization. In preliminary studies, in situ hybridization of brain slices indicated that galectin-8 is specifically expressed in the hypocampus, cerebellum, and brain stem, with little expression in the cortex (not shown). These findings suggest that unlike galectin-4, galectin-8 is an abundant protein that might play a role in certain brain functions.

Northern blot analysis of rat tissues was carried out and the results are shown in Table 1.

TABLE I

Tissue Distribution of galectin-8 mRNA according to Northern Blot Analysis.

| | |
|---|---|
| Lung | 100 |
| Liver | 43.4 |
| Cardiac muscle | 39.5 |
| Spleen | 36.3 |
| Hind limb Muscle | 31.6 |
| Brain | 12.6 |
| Fetus | 8.1 |

Figure 3:
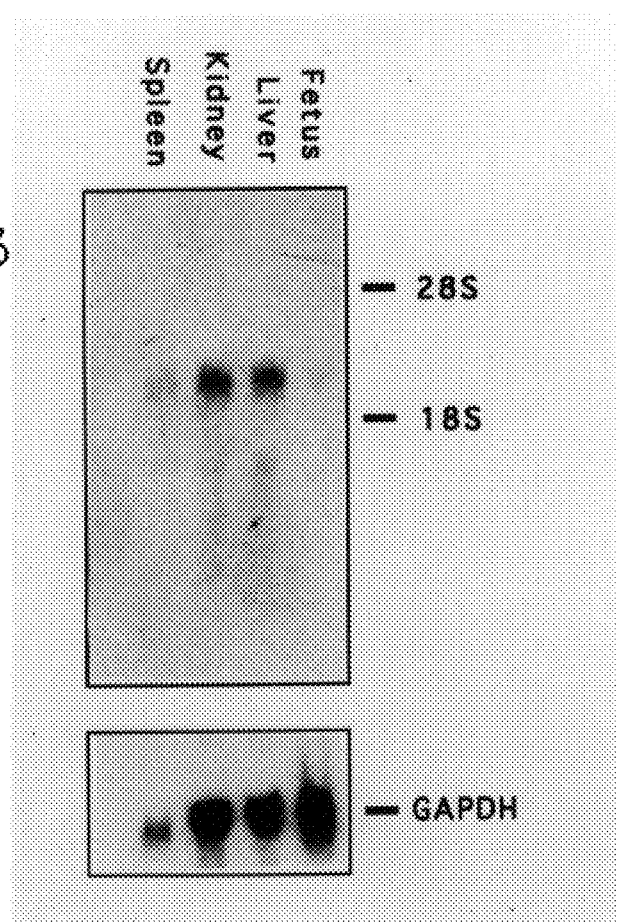
FIG. 3 shows Northern blot analysis of RNA from rat tissues probed with galectin-8 cDNA. Top, 30 μg of total RNA from the indicated tissues was electrophoresed, blotted, and probed with labeled galectin-8 PCR product as described in "Experimental Procedures". The migration of the 18S and 28S rRNA are marked. Bottom, the same blot was stripped and reblotted with cDNA encoding for GAPDH.

Total RNA from the indicated rat tissues was electrophoresed, blotted, and probed as described in legend to FIG. 3. The intensity of the signal corresponding to the galectin-8 probe was determined by densitometry and is presented as percentage of the strongest signal (normalized to GAPDH) which was obtained in lung (100%).

The expression of galectin-8 in different rat tissues was examined by Northern blots (FIG. 3). A single mRNA transcript of ~3 kb hybridized with galectin-8 PCR product probe. Unlike galectin-4, which is confined to intestine and stomach (12), galectin-8 mRNA is highly expressed in lung, and to a lower extent in liver, kidney, spleen, hind-limb, and cardiac muscle (FIG. 3, Table 1). Lower levels of expression were detected in brain and almost no expression was found in whole rat embryos.

EXAMPLE 7

Generation and purification of recombinant N-terminal (rgalectin-8nt) and C-terminal (rgalectin-8ct) domains of galectin-8.

To determine whether galectin-8nt has any sugar-binding activity, and whether galectin-8ct might function independently of its N-terminal half, galectin-8nt and galectin-8ct are amplified by PCR and proper restriction sites are introduced. Expression of each domain either as a GST-fusion protein or as tag-free domain are carried out as described above (Example 4). To express tag-free galectin-8ct the Met residue placed within the MCS of pET-3d is utilized as the start-site. Purification of galectin-8nt and galectin-8ct is carried out as described above (Example 4).

EXAMPLE 8

Generation of mammalian cells that overexpress galectin-8 in a transient or stable manner.

The cDNA coding for galectin-8 was introduced into four different eukaryotic high expression plasmids: pcDNA I Amp (Invitrogene); pREP8 (Invitrogene); pBPV-II, and pMAMneo (Clontec). The latter plasmid, having a dexamethasone-inducible MMTV-LTR promoter is of particular use if constitutive overexpression of galectin-8 induces growth arrest or prevents adhesion of the transfected cells. Sequencing of the vector/insert boundaries is carried out, to ensure proper integration of the insert.

a. Transient expression of galectin-8—Northern blot analysis of RNA and Western immunoblotting with lp-lec8 antibodies, has indicated that COS-7 cells express low levels of endogenous galectin-8. These cells are therefore appropriate targets to study transient expression of galectin-8. COS-7 cells are plated in DMEM/10% FCS at $2 \times 10^6$ cells /10 cm plate, 24 h before transfection. Cells are transfected with 10 μg of plasmid DNA using DEAE-dextran and DMSO-facilitated uptake according to standard procedures (modified by 0.1 mM chloriquine treatment). Cells are harvested 48–72 h thereafter, and the expressed galectin-8 is detected by Western immunoblotting with lp-lec8 or rgalectin-8 antibodies. Galectin-8 is purified by affinity-chromatography over lactosyl-Sepharose column, and by immunoaffinity chromatography using lp-lec8 or rgalectin-8 antibodies coupled to Sepharose as immunoadsorbent.

b. Stable expression of galectin-8—The above expression plasmids are used for stable transfection of galectin-8 DNA into Chinese Hamster Ovary (CHO) cells that have relatively low amount of endogenous galectin-8. Stable transfectants are identified by their ability to accumulate galectin-8 in the cytosol, or to secrete galectin-8 into the medium. Conditioned-medium is collected, concentrated by Amicon Centricon-10 micro concentrator, and lyophilized. Cytosolic extracts are prepared by boiling in "sample buffer" and the presence of galectin-8 is detected by immunoblotting with galectin-8 antibodies. Cells expressing the highest concentration of galectin-8 are further propagated.

EXAMPLE 9

Biological activity of whole rgalectin-8 and its individually-expressed N- or C-terminal domains To assess the functional need for two CRDs within the same polypeptide chain of galectin-8, the biological activity of rgalectin-8 is compared with that of its individually-expressed domains.

i. Hemagglutination activity of rgalectin-8, rgalectin-8nt and rgalectin-8ct is assayed as previously described (17). Rabbit erythrocytes are trypsin-treated and fixed with glutaraldehyde. Following washings in 0.1 M glycine/PBS and PBS, and proper dilution, hemagglutination activity of serial dilutions of rgalectin-8 is compared with those of rgalectin-8nt and rgalectin-8ct. If rgalectin-8, like galectin-1, is capable of forming homodimers, and if both CRDs of galectin-8 are capable of sugar binding, then rgalectin-8 is expected to express hemagglutination activity. If however rgalectin-8nt has reduced or no sugar-binding activity, and if rgalectin-8 fails to dimerize, then rgalectin-8, having a single functional CRD at the C-terminal domain, might fail to express hemagglutination activity. These results will implicate galectin-8 as having a function different from cross-linking glycoconjugates.

ii. Carbohydrate-binding specificity of whole galectin-8 and its individually-expressed domains is compared to previously determined specificity of other galectins, including galectin-4. To avoid possible alterations in the native structure of galectin-8 (e.g. due to carboxymethylation and iodination) 5 μg of purified rgalectin-8 (or individual domains) are incubated with 100 μl of lactosyl-Sepharose; conditions that result in quantitative binding of rgalectin-8. Binding specificity may be determined by the capacity of various saccharides (e.g. thiodigalactose, thiodiglucose) to inhibit binding of rgalectin-8 (or individual domains), when compared with lactose. If galectin8nt expresses, as predicted, altered or markedly reduced carbohydrate-binding activity, binding activity may be restored by site-directed mutagenesis, where the Ile-90 residue is mutated to Arg.

EXAMPLE 10

Site-directed mutagenesis.

Site-directed mutagenesis is carried out using "Altered Sites II in vitro mutagenesis systems" (Promega) according to the manufacturer's manual. First, Ile-90 is mutated to Arg to determine how such substitution affects hemagglutination activity and sugar binding specificity of rgalectin-8nt and whole galectin-8. Conversely, Arg-253, located within the WG-E-R motif at the C-terminal CRD may be mutated to Ile, and the effect of this mutation on the biological activity of galectin-8 is assessed. If Arg-253→Ile mutation markedly reduces or abolishes the in vitro biological activity of galectin-8, then the biological consequences of overexpression of this negative-dominant mutant will be compared with cells that overexpress the native form of galectin-8.

EXAMPLE 11

Sensitivity of rgalectin-8 to oxidation.

One whole mark of certain galectins is the sensitivity of their carbohydrate-binding activity to oxidation. Other studies suggest that for certain of these lectins the thiol-dependence may be ascribed to an artifact of the extraction procedure rather than an intrinsic requirement of the protein itself. To assess whether galectin-8 requires reducing environment to remain biologically active, the effects of various reductants and oxidants on the binding activity of galectin-8 to lactosyl-Sepharose are studied as described for other galectins. If galectin-8 activity is sensitive to oxidation, alkylation of rgalectin-8 may be carried out with iodoacetamide or with N-ethyl-maleimide. The modified product is then subjected to rechromatography over lactosyl-Sepharose column and is eluted with water. Alkylation, that stabilizes galectin-1, may preserve and stabilize rgalectin-8 activity (i.e. binding affinity to lactosyl-Sepharose), and enables increase of the half-life of rgalectin-8 and better study of its effects on cultured cells under the oxidizing environment of tissue culture medium.

EXAMPLE 12
Sensitivity of rgalectin-8 to proteolysis.

Preliminary experiments have indicated that endogenous mammalian galectin-8 is susceptible to proteolysis. To determine the physiological significance of this phenomena, pulse-chase experiments with $^{35}$S-labeled cells, followed by immunoprecipitation of the endogenous galectin-8, are carried out in CHO cells overexpressing galectin-8. $^{35}$S-labeled galectin-8 is precipitated with lp-lec8 or rgalectin-8 antibodies. The half-life of endogenous galectin-8 and the formation of in vivo degradation products are then evaluated. To distinguish proteolysis that occurs in vivo from one that occurs during extraction and purification, homogenization is carried out in the presence of trace amounts of $^{125}$I-labeled rgalectin-8.

EXAMPLE 13
Biological activity of galectin-8

The effects of galectin-8 on cell adhesion and on regulation of cellular growth are examined.

Effects of galectin-8 on cell adhesion

One of the well characterized effects of galectin-1 is its ability to inhibit myoblast adhesion to laminin (15). To determine whether galectin-8 shares a similar property, the effects of overexpression of galectin-8 on cell adhesion are studied. COS-7 cells are co-transfected with an expression vector for β-galactosidase (pSMβGal) at a 1:20 ratio to the galectin-8 vector. Cells expressing β-galactosidase are easily distinguished by a blue staining after histochemical reaction with X-gal, 36 h following transfection. Alterations in adhesion of blue cells as a function of time are monitored. Control cells are cotransfected with pSMβGal and pcDNA-IR (which contains an insert encoding for the insulin receptor). If positive results are obtained, thio-D-glucose (TDG) is added to inhibit lectin-carbohydrate interactions and study the contribution of the carbohydrate-binding domains to this effect.

In an alternative approach CHO cells, transfected with the pMAMneo-galectin-8 plasmid (which has a dexamethasone-inducible MMTV-LTR promoter) is used. Their adhesive properties to the culture dish, before and after induction, are compared. If positive results are obtained, the effects of TDG on cell adhesion and the effects of exogenously-added rgalectin-8 on non-induced cells are determined.

Function of galectin-8 as a cytostatic factor and cell growth regulator.

mGBP, a single-domain homologue of galectin-8, was shown to be a cell growth-regulatory molecule and a cytostatic factor that binds to a specific cell surface receptor (8). To determine whether galectin-8 fulfills a similar role, since galectin-8 is expressed in rat liver, rat hepatoma (Fao) cells are used as a model system. Another model is mouse embryo fibroblasts (MEF), that were already shown to be subjected to the growth inhibitory action of mGBP (8). Growth inhibition induced by purified rgalectin-8 is assessed by several parameters:

i. Direct counting of logarithmically growing cells, incubated for increasing time periods with increasing concentrations of native or denatured (control) rgalectin-8. Cell viability is assessed calorimetrically utilizing the neutral red uptake assay.

ii. Inhibition of DNA synthesis is monitored by [$^3$H] thymidine incorporation into control, and rgalectin-8-treated cells.

iii. Change in population distribution, due to inhibition of cell growth, is assessed by FACS analysis.

iv. Changes in cell morphology are monitored in cells grown on cover slips. Following treatment, cells are washed, fixed, and viewed by Nomarski interference contrast microscopy.

The reversibility of the galectin-8 effects on these parameters may then be evaluated. The relation between sugar binding and the biological activity of rgalectin-8 may be further assessed by the ability of 10 mM TDG to compete for rgalectin-8 binding. Successful results lead to the second stage of the study, where it is determined whether growth inhibition is related to the growth state, as is in the case of mGBP and cytokines. For that purpose cells stationed in Go by serum starvation, and cells rescued from Go by serum stimulation, are treated with galectin-8 for different times, and its potency to attenuate or inhibit cell growth is evaluated.

Figure 7:
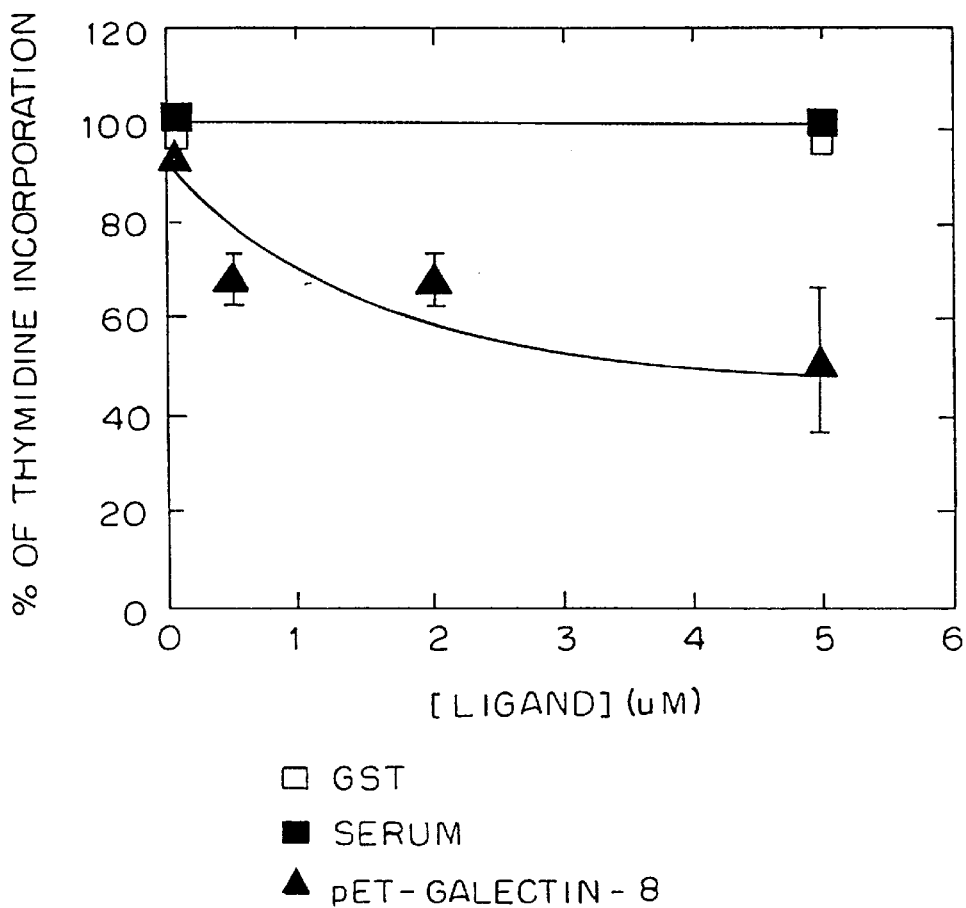
FIG. 7 shows inhibition by recombinant galectin-8 of serum-induced $^3$H-thymidine incorporation into DNA. $^3$H-Thymidine incorporation into DNA was examined as follows: Confluent CHO cells, grown in 24-well trays (Costar), were starved for 48 hours in serum-free medium. Medium containing 10% fetal calf serum was added to the cells in the presence of rgalectin-8 at the indicated concentrations, and the cells were incubated for 14.5 hours at 37° C. The medium was then washed, and the cells were incubated for 2 hours at 37° C. in 1 ml of serum-free medium containing 1% BSA, 20 mM Hepes (pH 7.5) and 0.5 μCi/ml [$^3$H]-thymidine. At the end of incubation, the solution was removed, cells were washed 3 times in ice-cold PBS and incubated for 30 min at 4° C. in 0.5 ml ice-cold 7.5% trichloroacetic acid. The pellets were washed twice with 98% ice-cold ethanol, dissolved in 0.6 ml of 0.1 M NaOH, and counted using scintillation cocktail containing xylene and Lumax (6:4 ratio, respectively).

Inhibition of DNA synthesis was monitored in control and rgalectin-8-treated CHO cells as described in the legend to FIG. 7. It can be seen that rgalectin-8 inhibits serum-induced [$^3$H] thymidine incorporation in a dose-dependent manner. Half-maximal effects are obtained at 0.5 $\mu$M and maximal effects at 2 $\mu$M rgalectin-8, GST alone is without effect.

EXAMPLE 14
Use of galectin-8 antibodies as diagnostic tools for neoplastic transformation.

Suitable compositions prepared by well-known standard procedures, containing anti-galectin-8 antibodies may be used to detect overexpression of this protein following neoplastic transformation in general, and in metastatic melanoma cells in particular, and accordingly, to determine whether overexpression of galectin-8 can serve as an early signal for neoplastic transformation, and/or the development of metastatic melanoma. Thus, the anti-galectin-8 antibodies mat serve as a diagnostic tool for early detection of the above disease. Moreover, the presence of a subject's own anti-galectin-8 antibodies can also serve as such a diagnostic tool, which endogenous anti-galectin-8 antibodies may be assayed with purified galectin-8.

REFERENCES

1. Sharon, N. (1993) *TIBS* 18, 221–225.

2. Barondes, S. H., Castronovo, V., Cooper, D. N., Cummings, R. D., Drickamer, K., Feizi, T., Gitt, M. A., Hirabayashi, J., Hughes, C., Kasai, K. et. al. (1994) *Cell* 76, 597–598.

3. Barondes, S. H., Cooper, D. N. W., Gitt, M. A., and Leffler, H. (1994) *J. Biol. Chem.* 269, 20807–20810.

4. Hirabayashi, J. and Kasai, K. (1991) *J Biol Chem* 266, 23648–23653.

5. Lobsanov, Y. D., Gitt, M. A., Leffler, H., Barondes, S. H., and Rini, J. M. (1993) *J Biol Chem* 268, 27034–27038.

6. Tracey, B. M., Feizi, T., Abbott, W. M., Carruthers, R. A., Green, B. N. and Lawson, A. M. (1992) *J Biol Chem* 267, 10342–10347.

7. Cooper, D. N., Massa, S. M. and Barondes, S. H. (1991) *J Cell Biol* 115, 1437–1448.

8. Wells, V., and Mallucci, L. (1991) *Cell* 64, 91–97.

9. Yamaoka, K., Ohno, S., Kawasaki, H. and Suzuki, K. (1991) *Biochem Biophys Res Commun* 179, 272–279.

10. Poirier, F., Timmons, P. M., Chan, C. T., Guenet, J. L. and Rigby, P. W. (1992) *Development* 115, 143–155.

11. Ochieng, J., Platt, D., Tait, L., Hogan, V., Raz, T., Carmi, P., and Raz, A. (1993) *Biochemistry* 32, 4455–4460.

12. Oda, Y., Herrmann, J., Gitt, M. A., Turck, C. W., Burlingame, A. L., Barondes, S. H. and Leffler, H. (1993) *J Biol Chem* 268, 5929–5939.

13. Hirabayashi, J., Satoh, M. and Kasai, K. (1992) *J Biol Chem* 267, 15485–15490.

14. Lamphere, L. and Lienhard, G. E. (1992) *Endocrinology* 131, 2196–2202.

15. Cooper, D. N., and Barondes, S. H. (1990) *J Cell Biol* 110, 1681–1691.

16. Sambrook, J., Fritsch, E. F., and Maniatis, T. *Molecular Cloning, a laboratory manual* (Cold Spring Harbor Laboratory Press, 1989).

17. Lis, H., and Sharon, N. (1972) *Methods Enzymol.* 28, 360–368.

I claim:

1. A sugar-binding and cell agglutinating molecule selected from the group consisting of:

(i) the protein galectin-8 having the amino acid sequence of SEQ ID NO:2;

(ii) a protein other than the protein of (i), extracted from a mammal of a species other than rat and which has sugar-binding ability and the ability to agglutinate formaldehyde-fixed, trypsin-treated rabbit erythrocyte, which protein is encoded by DNA which hybridizes to the DNA of SEQ ID NO:1 under moderately stringent conditions carried out at 42° C. in 50% formamide 5×SSC with washes at 60° C. in 0.1×SSC, 0.1% SDS;

(iii) a protein other than the protein of (i), extracted from a mammal of a species other than rat and which has sugar-binding ability and the ability to agglutinate formaldehyde-fixed, trypsin-treated rabbit erythrocyte, which protein is bound by an antibody specific for an epitope in the region of amino acids 153–184 of SEQ ID NO:2; and (iv) a fragment of (i), (ii) or (iii) which has sugar-binding ability and the ability to agglutinate formaldehyde-fixed, trypsin-treated rabbit erythrocyte.

2. A molecule in accordance with claim 1, comprising the galectin-8 protein of (i).

3. An isolated recombinant DNA molecule comprising a nucleotide sequence encoding a molecule in accordance with claim 1.

4. An isolated DNA molecule in accordance with claim 3, comprising the nucleotide sequence of nucleotides 121–1068 of SEQ ID NO:1.

5. An isolated DNA molecule in accordance with claim 3, comprising the nucleotide sequence of the coding region of the galectin-8 gene.

6. A recombinant expression vector comprising a recombinant DNA molecule in accordance with claim 3.

7. A host cell containing a recombinant expression vector in accordance with claim 6.

8. A process for producing a sugar-binding molecule, comprising culturing a host cell according to claim 7 under conditions promoting expression, and isolating the sugar-binding molecule expressed thereby.

9. An antibody specific for an epitope in the region of 153–184 of SEQ ID NO:2.

* * * * *

SEQUENCE LISTING (1) GENERAL INFORMATION:

(iii) NUMBER OF SEQUENCES: 19

(2) INFORMATION FOR SEQ ID NO:1:

(i) SEQUENCE CHARACTERISTICS:
      (A) LENGTH: 1247 base pairs
      (B) TYPE: nucleic acid
      (C) STRANDEDNESS: single
      (D) TOPOLOGY: linear (ii) MOLECULE TYPE: cDNA (ix) FEATURE:
      (A) NAME/KEY: CDS
      (B) LOCATION: 121..1068

(xi) SEQUENCE DESCRIPTION: SEQ ID NO:1:

```
AATTCCCCCC CTGGCTGGGG ACAAGTTATT ACTTTGAGTA ATCCTTAAAT GAAGAGTGGG        60

TAAAGCCCAT ATACGGAAGA GAGACTCCAG TCAACAATAT CAATAAGTTG AAGAAGAAAA       120

ATG TTG TCC TTA AGC AAT CTA CAA AAT ATC ATC TAT AAC CCG ACA ATC        168
Met Leu Ser Leu Ser Asn Leu Gln Asn Ile Ile Tyr Asn Pro Thr Ile
  1               5                  10                  15

CCC TAT GTC AGT ACC ATT ACT GAG CAG TTG AAG CCT GGC TCT TTG ATC        216
Pro Tyr Val Ser Thr Ile Thr Glu Gln Leu Lys Pro Gly Ser Leu Ile
             20                  25                  30

GTG ATC CGT GGC CAT GTT CCT AAA GAT TCA GAA AGA TTC CAA GTA GAC        264
Val Ile Arg Gly His Val Pro Lys Asp Ser Glu Arg Phe Gln Val Asp
         35                  40                  45

TTT CAG CAT GGC AAC AGC CTG AAG CCG AGA GCT GAT GTG GCC TTC CAC        312
Phe Gln His Gly Asn Ser Leu Lys Pro Arg Ala Asp Val Ala Phe His
     50                  55                  60

TTT AAC CCT CGC TTC AAA AGG TCC AAC TGC ATT GTT TGT AAC ACA CTG        360
Phe Asn Pro Arg Phe Lys Arg Ser Asn Cys Ile Val Cys Asn Thr Leu
 65                  70                  75                  80

ACA AAT GAG AAA TGG GGC TGG GAG GAG ATC ACC CAC GAC ATG CCT TTC        408
Thr Asn Glu Lys Trp Gly Trp Glu Glu Ile Thr His Asp Met Pro Phe
                 85                  90                  95

AGA AAA GAA AAG TCC TTT GAG ATT GTG ATC ATG GTG CTA AAG AAC AAA        456
Arg Lys Glu Lys Ser Phe Glu Ile Val Ile Met Val Leu Lys Asn Lys
            100                 105                 110

TTC CAC GTG GCT GTG AAT GGA AAG CAC ATT CTG CTG TAT GCC CAC AGG        504
Phe His Val Ala Val Asn Gly Lys His Ile Leu Leu Tyr Ala His Arg
        115                 120                 125

ATC AAC CCA GAG AAG ATA GAC ACA CTG GGC ATC TTC GGC AAA GTG AAC        552
Ile Asn Pro Glu Lys Ile Asp Thr Leu Gly Ile Phe Gly Lys Val Asn
    130                 135                 140
```

-continued

```
ATT CAC TCC ATC GGG TTC AGA TTC AGC TCG GAT TTA CAG AGT ATG GAA       600
Ile His Ser Ile Gly Phe Arg Phe Ser Ser Asp Leu Gln Ser Met Glu
145                 150                 155                 160

ACA TCT ACT CTG GGA CTG ACA CAG ATA AGT AAA GAA AAT ATA CAA AAG       648
Thr Ser Thr Leu Gly Leu Thr Gln Ile Ser Lys Glu Asn Ile Gln Lys
                165                 170                 175

TCT GGC AAG CTC CAT TTG AGC CTG CCA TTT GAA GCA AGG TTG AAT GCC       696
Ser Gly Lys Leu His Leu Ser Leu Pro Phe Glu Ala Arg Leu Asn Ala
            180                 185                 190

TCC ATG GGC CCT GGA CGA ACC GTT GTC GTT AAA GGA GAA GTG AAT ACA       744
Ser Met Gly Pro Gly Arg Thr Val Val Val Lys Gly Glu Val Asn Thr
        195                 200                 205

AAT GCC ACA AGC TTT AAT GTT GAC CTA GTG GCA GGA AGG TCA AGG GAT       792
Asn Ala Thr Ser Phe Asn Val Asp Leu Val Ala Gly Arg Ser Arg Asp
    210                 215                 220

ATC GCT CTG CAC TTG AAC CCA CGC CTG AAT GTG AAA GCG TTT GTA AGA       840
Ile Ala Leu His Leu Asn Pro Arg Leu Asn Val Lys Ala Phe Val Arg
225                 230                 235                 240

AAC TCC TTT CTT CAG GAT GCC TGG GGA GAA GAG GAG AGA AAC ATT ACC       888
Asn Ser Phe Leu Gln Asp Ala Trp Gly Glu Glu Glu Arg Asn Ile Thr
                245                 250                 255

TGC TTC CCA TTT AGT TCT GGG ATG TAC TTT GAG ATG ATA ATT TAC TGT       936
Cys Phe Pro Phe Ser Ser Gly Met Tyr Phe Glu Met Ile Ile Tyr Cys
                260                 265                 270

GAT GTC CGA GAG TTC AAG GTT GCA GTA AAT GGT GTG CAC AGC CTG GAG       984
Asp Val Arg Glu Phe Lys Val Ala Val Asn Gly Val His Ser Leu Glu
            275                 280                 285

TAC AAG CAC AGA TTT AAA GAC CTA AGC AGC ATC GAC ACA CTA GCA GTT      1032
Tyr Lys His Arg Phe Lys Asp Leu Ser Ser Ile Asp Thr Leu Ala Val
        290                 295                 300

GAT GGC GAT ATC CGT TTG CTG GAT GTA AGG AGC TGG TAGCTATCAT           1078
Asp Gly Asp Ile Arg Leu Leu Asp Val Arg Ser Trp
305                 310                 315

GACTGCCAGA ACCCTGGAAA TACAAAATGG CTTATCCGAT ACTGGCCATG TCAAATGCAT    1138

CTCGCTTTCA CCACATTGTT ATACTGTTAA GTTGAGCTCG CACAACATCA AGTCCTACTG    1198

GTGTTGTCAG GCCTGGCCAT GCAGTGTGGC TACCTCTGAA TTCCCAGGA               1247
```

(2) INFORMATION FOR SEQ ID NO:2:

(i) SEQUENCE CHARACTERISTICS:
        (A) LENGTH: 316 amino acids
        (B) TYPE: amino acid
        (D) TOPOLOGY: linear (ii) MOLECULE TYPE: protein (xi) SEQUENCE DESCRIPTION: SEQ ID NO:2:

```
Met Leu Ser Leu Ser Asn Leu Gln Asn Ile Ile Tyr Asn Pro Thr Ile
1               5                   10                  15

Pro Tyr Val Ser Thr Ile Thr Glu Gln Leu Lys Pro Gly Ser Leu Ile
                20                  25                  30

Val Ile Arg Gly His Val Pro Lys Asp Ser Glu Arg Phe Gln Val Asp
            35                  40                  45

Phe Gln His Gly Asn Ser Leu Lys Pro Arg Ala Asp Val Ala Phe His
        50                  55                  60

Phe Asn Pro Arg Phe Lys Arg Ser Asn Cys Ile Val Cys Asn Thr Leu
65                  70                  75                  80

Thr Asn Glu Lys Trp Gly Trp Glu Glu Ile Thr His Asp Met Pro Phe
                85                  90                  95
```

-continued

```
Arg Lys Glu Lys Ser Phe Glu Ile Val Ile Met Val Leu Lys Asn Lys
            100                 105                 110

Phe His Val Ala Val Asn Gly Lys His Ile Leu Leu Tyr Ala His Arg
            115                 120                 125

Ile Asn Pro Glu Lys Ile Asp Thr Leu Gly Ile Phe Gly Lys Val Asn
            130                 135                 140

Ile His Ser Ile Gly Phe Arg Phe Ser Ser Asp Leu Gln Ser Met Glu
145                 150                 155                 160

Thr Ser Thr Leu Gly Leu Thr Gln Ile Ser Lys Glu Asn Ile Gln Lys
                    165                 170                 175

Ser Gly Lys Leu His Leu Ser Leu Pro Phe Glu Ala Arg Leu Asn Ala
                    180                 185                 190

Ser Met Gly Pro Gly Arg Thr Val Val Lys Gly Glu Val Asn Thr
            195                 200                 205

Asn Ala Thr Ser Phe Asn Val Asp Leu Val Ala Gly Arg Ser Arg Asp
            210                 215                 220

Ile Ala Leu His Leu Asn Pro Arg Leu Asn Val Lys Ala Phe Val Arg
225                 230                 235                 240

Asn Ser Phe Leu Gln Asp Ala Trp Gly Glu Glu Arg Asn Ile Thr
                    245                 250                 255

Cys Phe Pro Phe Ser Ser Gly Met Tyr Phe Glu Met Ile Ile Tyr Cys
            260                 265                 270

Asp Val Arg Glu Phe Lys Val Ala Val Asn Gly Val His Ser Leu Glu
            275                 280                 285

Tyr Lys His Arg Phe Lys Asp Leu Ser Ser Ile Asp Thr Leu Ala Val
            290                 295                 300

Asp Gly Asp Ile Arg Leu Leu Asp Val Arg Ser Trp
305                 310                 315

(2) INFORMATION FOR SEQ ID NO:3:

(i) SEQUENCE CHARACTERISTICS:
        (A) LENGTH: 135 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:3:

Met Ala Gly Gly Leu Val Ala Ser Asn Leu Asn Leu Lys Pro Gly Glu
1               5                   10                  15

Cys Leu Arg Val Arg Gly Glu Val Ala Pro Asp Ala Lys Ser Glu Val
            20                  25                  30

Leu Asn Leu Gly Lys Asp Ser Asn Asn Leu Cys Glu His Glu Asn Pro
            35                  40                  45

Arg Glu Asn Ala His Gly Asp Ala Asn Thr Ile Val Cys Asn Ser Lys
            50                  55                  60

Asp Gly Gly Ala Trp Gly Thr Glu Gln Arg Glu Ala Val Phe Pro Glu
65                  70                  75                  80

Gln Pro Gly Ser Val Ala Glu Val Cys Ile Thr Phe Asp Gln Ala Asn
            85                  90                  95

Glu Thr Val Lys Leu Pro Asp Gly Tyr Glu Phe Lys Ser Pro Asn Arg
            100                 105                 110

Leu Asn Leu Glu Ala Ile Asn Tyr Met Ala Ala Asp Gly Asp Phe Lys
            115                 120                 125

Ile Lys Cys Val Ala Phe Asp
```

```
          130              135
```

(2) INFORMATION FOR SEQ ID NO:4:

(i) SEQUENCE CHARACTERISTICS:
        (A) LENGTH: 132 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:4:

```
Met Thr Gly Glu Leu Glu Val Lys Asn Met Asp Met Lys Pro Gly Ser
1               5                   10                  15

Thr Leu Lys Ile Thr Gly Ser Ile Ala Asp Gly Thr Asp Gly Glu Val
            20                  25                  30

Ile Asn Leu Gly Gln Gly Thr Asp Lys Leu Asn Glu His Glu Asn Pro
            35                  40                  45

Arg Glu Ser Glu Ser Thr Ile Val Cys Asn Ser Leu Asp Gly Ser Asn
        50                  55                  60

Trp Gly Gln Glu Gln Arg Glu Asp His Leu Cys Glu Ser Pro Gly Ser
65                  70                  75                  80

Glu Val Lys Phe Thr Val Thr Phe Glu Ser Asp Lys Glu Lys Val Lys
                85                  90                  95

Leu Pro Asp Gly His Glu Leu Thr Ser Pro Asn Arg Leu Gly His Ser
            100                 105                 110

His Leu Ser Tyr Leu Ser Trp Arg Gly Gly Phe Asn Pro Ser Ser Phe
            115                 120                 125

Lys Leu Lys Glu
    130
```

(2) INFORMATION FOR SEQ ID NO:5:

(i) SEQUENCE CHARACTERISTICS:
        (A) LENGTH: 135 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:5:

```
Val Pro Tyr Asp Met Pro Leu Pro Gly Gly Val Met Pro Arg Met Leu
1               5                   10                  15

Ile Thr Ile Ile Gly Thr Val Lys Pro Asn Ala Asn Ser Glu Thr Leu
            20                  25                  30

Asn Glu Lys Lys Gly Asn Asp Ile Ala Glu His Glu Asn Pro Arg Glu
            35                  40                  45

Asn Glu Asn Asn Arg Arg Val Ile Val Cys Asn Thr Lys Gln Asp Asn
        50                  55                  60

Asn Trp Gly Arg Glu Glu Arg Gln Ser Ala Phe Pro Glu Glu Ser Gly
65                  70                  75                  80

Lys Pro Glu Lys Ile Gln Val Leu Val Glu Ala Asp His Glu Lys Val
                85                  90                  95

Ala Val Asn Asp Val His Leu Leu Gln Tyr Asn His Arg Met Lys Asn
            100                 105                 110

Leu Arg Glu Ile Ser Gln Leu Gly Ile Ile Gly Asp Ile Thr Leu Thr
            115                 120                 125

Ser Ala Ser His Ala Met Ile
```

```
                130                 135

(2) INFORMATION FOR SEQ ID NO:6:

(i) SEQUENCE CHARACTERISTICS:
         (A) LENGTH: 177 amino acids
         (B) TYPE: amino acid
         (C) STRANDEDNESS: single
         (D) TOPOLOGY: linear (ii) MOLECULE TYPE: peptide (xi) SEQUENCE DESCRIPTION: SEQ ID NO:6:

Met Ala Tyr Val Pro Ala Pro Gly Tyr Gln Pro Thr Tyr Asn Pro Thr
1               5                  10                  15

Leu Pro Tyr Lys Arg Pro Ile Pro Gly Gly Leu Ser Val Gly Met Ser
            20                  25                  30

Ile Tyr Ile Gln Gly Ile Ala Lys Asp Asn Met Arg Arg Glu His Val
        35                  40                  45

Asn Glu Ala Val Gly Gln Asp Glu Gly Ala Asp Ile Ala Glu His Glu
    50                  55                  60

Asn Pro Arg Glu Asp Gly Trp Asp Lys Val Val Phe Asn Thr Met Gln
65                  70                  75                  80

Ser Gly Gln Trp Gly Lys Glu Glu Lys Lys Lys Ser Met Pro Glu Gln
                85                  90                  95

Lys Gly His His Glu Glu Leu Val Glu Met Val Met Ser Glu His Lys
            100                 105                 110

Lys Val Val Val Asn Gly Thr Pro Phe Tyr Glu Tyr Gly His Arg Leu
        115                 120                 125

Pro Leu Gln Met Val Thr His Leu Gln Val Asp Gly Asp Leu Glu Leu
    130                 135                 140

Gln Ser Ile Asn Phe Leu Gly Gly Gln Pro Ala Ala Ser Gln Tyr Pro
145                 150                 155                 160

Gly Thr Met Thr Ile Pro Ala Tyr Pro Ser Ala Gly Tyr Asn Pro Pro
                165                 170                 175

Gln (2) INFORMATION FOR SEQ ID NO:7:

(i) SEQUENCE CHARACTERISTICS:
         (A) LENGTH: 147 amino acids
         (B) TYPE: amino acid
         (C) STRANDEDNESS: single
         (D) TOPOLOGY: linear (ii) MOLECULE TYPE: peptide (xi) SEQUENCE DESCRIPTION: SEQ ID NO:7:

Met Asn Ser Leu Pro Val Met Ala Gly Pro Pro Ile Phe Asn Pro Pro
1               5                  10                  15

Val Pro Tyr Val Gly Thr Leu Gln Gly Gly Leu Thr Ala Arg Arg Thr
            20                  25                  30

Ile Ile Ile Lys Gly Tyr Val Leu Pro Thr Ala Lys Asn Ile Ile Ile
        35                  40                  45

Asn Glu Lys Val Gly Ser Thr Gly Asp Ile Ala Glu His Met Asn Pro
    50                  55                  60

Arg Ile Gly Asp Cys Val Val Arg Asn Ser Tyr Met Asn Gly Ser Trp
65                  70                  75                  80

Gly Ser Glu Glu Arg Lys Ile Pro Tyr Asn Pro Glu Gly Ala Gly Gln
                85                  90                  95
```

```
Phe Glu Asp Leu Ser Ile Arg Cys Gly Thr Asp Arg Glu Lys Val Phe
            100                 105                 110

Ala Asn Gly Gln His Leu Phe Asp Arg Ser His Arg Phe Gln Ala Pro
            115                 120                 125

Gln Arg Val Asp Met Leu Glu Ile Lys Gly Asp Ile Thr Leu Ser Tyr
            130                 135                 140

Val Gln Ile
145
```

(2) INFORMATION FOR SEQ ID NO:8:

(i) SEQUENCE CHARACTERISTICS:
        (A) LENGTH: 146 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:8:

```
Met Ser Ala Glu Glu Pro Lys Ser Tyr Pro Val Pro Tyr Arg Ser Val
1               5                   10                  15

Leu Gln Glu Lys Leu Glu Pro Gly Gln Thr Leu Ile Val Lys Gly Ser
            20                  25                  30

Thr Ile Asp Glu Ser Gln Arg Glu Thr Ile Asn Leu His Ser Lys Thr
            35                  40                  45

Ala Asp Phe Ser Gly Asn Asp Val Pro Leu His Val Ser Val Arg Glu
        50                  55                  60

Asp Glu Gly Lys Ile Val Leu Asn Ser Phe Ser Asn Gly Glu Trp Gly
65                  70                  75                  80

Lys Glu Glu Arg Lys Ser Asn Pro Ile Lys Lys Gly Asp Ser Glu Asp
                85                  90                  95

Ile Arg Ile Arg Ala His Asp Asp Arg Glu Gln Ser Ile Val Asp His
                100                 105                 110

Lys Glu Phe Lys Asp Tyr Glu His Arg Leu Pro Leu Ser Ser Ile Ser
            115                 120                 125

His Leu Ser Ile Asp Gly Asp Leu Tyr Leu Asn His Val His Trp Gly
            130                 135                 140

Gly Lys
145
```

(2) INFORMATION FOR SEQ ID NO:9:

(i) SEQUENCE CHARACTERISTICS:
        (A) LENGTH: 131 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:9:

```
Pro Val Pro Tyr Glu Ser Gly Leu Ala Asn Gly Leu Pro Val Gly Lys
1               5                   10                  15

Ser Leu Leu Val Phe Gly Thr Val Glu Lys Lys Ala Lys Arg Glu His
            20                  25                  30

Val Asn Leu Leu Arg Lys Asn Gly Asp Ile Ser Glu His Glu Asn Pro
            35                  40                  45

Arg Glu Asp Glu Lys His Val Val Arg Asn Ser Leu Ala Ala Asn Glu
50                  55                  60
```

```
Trp Gly Asn Glu Glu Arg Glu Gly Lys Asn Pro Glu Glu Lys Gly Val
 65                  70                  75                  80

Gly Glu Asp Leu Val Ile Gln Asn Glu Glu Tyr Ala Glu Gln Val Phe
                 85                  90                  95

Val Asn Gly Glu Arg Tyr Ile Ser Arg Ala His Arg Ala Asp Pro His
                100                 105                 110

Asp Ile Ala Gly Leu Gln Ile Ser Gly Asp Ile Glu Leu Ser Gly Ile
            115                 120                 125

Gln Ile Gln
        130
```

(2) INFORMATION FOR SEQ ID NO:10:

(i) SEQUENCE CHARACTERISTICS:
        (A) LENGTH: 184 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:10:

```
Met Leu Ser Leu Ser Asn Leu Gln Asn Ile Ile Tyr Asn Pro Thr Ile
 1               5                  10                  15

Pro Tyr Val Ser Thr Leu Thr Glu Gln Leu Lys Pro Gly Ser Leu Ile
                 20                  25                  30

Val Ile Arg Gly His Val Pro Lys Asp Ser Glu Arg Glu Gln Val Asp
             35                  40                  45

Glu Gln His Gly Asn Ser Leu Lys Pro Arg Ala Asp Val Ala Glu His
         50                  55                  60

Glu Asn Pro Arg Glu Lys Arg Ser Asn Cys Ile Val Cys Asn Thr Leu
 65                  70                  75                  80

Thr Asn Glu Lys Trp Gly Trp Glu Glu Ile Thr His Asp Met Pro Glu
                 85                  90                  95

Arg Lys Glu Lys Glu Glu Ile Val Ile Met Val Leu Lys Asn Lys
                100                 105                 110

Glu His Val Ala Val Asn Gly Lys His Ile Leu Leu Tyr Ala His Arg
            115                 120                 125

Ile Asn Pro Glu Lys Ile Asp Thr Leu Gly Ile Phe Gly Lys Val Asn
130                 135                 140

Ile His Ser Ile Gly Phe Arg Phe Ser Asp Leu Gln Ser Met Glu
145                 150                 155                 160

Thr Ser Thr Leu Gly Leu Thr Gln Ile Ser Lys Glu Asn Ile Gln Lys
                165                 170                 175

Ser Gly Lys Leu His Leu Ser Leu
            180
```

(2) INFORMATION FOR SEQ ID NO:11:

(i) SEQUENCE CHARACTERISTICS:
        (A) LENGTH: 132 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:11:

```
Pro Glu Glu Ala Arg Leu Asn Ala Ser Met Gly Pro Gly Arg Thr Val
 1               5                  10                  15
```

```
Val Val Lys Gly Glu Val Asn Thr Asn Ala Thr Ser Glu Asn Val Asp
         20                  25                  30

Leu Val Ala Gly Arg Ser Arg Asp Ile Ala Ile His Ile Asn Pro Arg
         35                  40                  45

Ile Asn Val Lys Ala Phe Val Arg Asn Ser Phe Leu Gln Asp Ala Trp
         50                  55                  60

Gly Glu Glu Glu Arg Asn Ile Thr Cys Phe Pro Glu Ser Ser Gly Met
65                       70                  75                  80

Tyr Glu Glu Met Ile Ile Tyr Cys Asp Val Arg Glu Glu Lys Val Ala
                 85                  90                  95

Val Asn Gly Val His Ser Leu Glu Tyr Lys His Arg Phe Lys Asp Leu
             100                 105                 110

Ser Ser Ile Asp Thr Leu Ala Val Asp Gly Asp Ile Arg Leu Leu Asp
             115                 120                 125

Val Arg Ser Trp
         130
```

(2) INFORMATION FOR SEQ ID NO:12:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:12:

```
Cys Tyr Ala Ser Ile Asn Phe Gln Lys Gln Pro Glu Asp Arg Gln
1               5                   10                  15
```

(2) INFORMATION FOR SEQ ID NO:13:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:13:

CCCGACAATC CCCTATGTCA GTACC                                      25

(2) INFORMATION FOR SEQ ID NO:14:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:14:

GCATGGCCAG GCCTGACAAC A                                        21

(2) INFORMATION FOR SEQ ID NO:15:

(i) SEQUENCE CHARACTERISTICS:
        (A) LENGTH: 30 base pairs
        (B) TYPE: nucleic acid
        (C) STRANDEDNESS: single
        (D) TOPOLOGY: linear -continued (ii) MOLECULE TYPE: cDNA (xi) SEQUENCE DESCRIPTION: SEQ ID NO:15:

GGGGGGGGAT CCATGTTGTC CTTAAGCAAT                    30

(2) INFORMATION FOR SEQ ID NO:16:

(i) SEQUENCE CHARACTERISTICS:
       (A) LENGTH: 27 base pairs
       (B) TYPE: nucleic acid
       (C) STRANDEDNESS: single
       (D) TOPOLOGY: linear (ii) MOLECULE TYPE: cDNA (xi) SEQUENCE DESCRIPTION: SEQ ID NO:16:

GGGGGGCATA TGTTGTCCTT AAGCAAT                       27

(2) INFORMATION FOR SEQ ID NO:17:

(i) SEQUENCE CHARACTERISTICS:
       (A) LENGTH: 30 base pairs
       (B) TYPE: nucleic acid
       (C) STRANDEDNESS: single
       (D) TOPOLOGY: linear (ii) MOLECULE TYPE: cDNA (xi) SEQUENCE DESCRIPTION: SEQ ID NO:17:

GGGGGGGGAT CCGCCATTTT GTATTTCCAG                    30

(2) INFORMATION FOR SEQ ID NO:18:

(i) SEQUENCE CHARACTERISTICS:
       (A) LENGTH: 16 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO:18:

Cys Gln Ile Ser Lys Glu Thr Ile Gln Lys Ser Gly Lys Leu His Leu
1               5                   10                  15

(2) INFORMATION FOR SEQ ID NO:19:

(i) SEQUENCE CHARACTERISTICS:
       (A) LENGTH: 6 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO:19:

His Phe Asn Pro Arg Leu
1               5